(12) United States Patent
Takahashi et al.

(10) Patent No.: US 8,876,702 B2
(45) Date of Patent: Nov. 4, 2014

(54) ELECTRONIC ENDOSCOPE IN WHICH STATIC-PROTECTIVE MEMBER IS PROVIDED IN DISTAL END PORTION OF INSERTION PORTION

(71) Applicant: Olympus Medical Systems Corp., Tokyo (JP)

(72) Inventors: Tomohisa Takahashi, Hachioji (JP); Hironobu Ichimura, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/909,463

(22) Filed: Jun. 4, 2013

(65) Prior Publication Data

US 2013/0303853 A1 Nov. 14, 2013

Related U.S. Application Data

(63) Continuation of application No. PCT/JP2012/070655, filed on Aug. 14, 2012.

(30) Foreign Application Priority Data

Dec. 7, 2011 (JP) .................................. 2011-268189

(51) Int. Cl.
*A61B 1/05* (2006.01)
*G02B 23/24* (2006.01)
*A61B 1/00* (2006.01)
*A61B 1/005* (2006.01)
*A61B 1/12* (2006.01)

(52) U.S. Cl.
CPC ............. *A61B 1/000096* (2013.01); *A61B 1/05* (2013.01); *G02B 23/2484* (2013.01); *A61B 1/00114* (2013.01); *A61B 1/00124* (2013.01); *A61B 1/0051* (2013.01); *A61B 1/127* (2013.01); *G02B 23/2476* (2013.01); *G02B 2207/121* (2013.01); *A61B 1/0008* (2013.01)
USPC ............ 600/134; 600/129; 600/130; 600/169

(58) Field of Classification Search
CPC ............. A61B 1/0008; A61B 1/00071; A61B 1/00096; A61B 1/05; A61B 1/127; G02B 23/2492; G02B 23/2484
USPC .......................... 600/134, 129, 130, 176, 169
See application file for complete search history.

(56) References Cited

U.S. PATENT DOCUMENTS 4,779,130 A * 10/1988 Yabe ............................... 348/76
4,895,138 A * 1/1990 Yabe .............................. 600/110

(Continued)

FOREIGN PATENT DOCUMENTS

JP 05-154101 A 6/1993
JP 05-154102 A 6/1993

(Continued)

*Primary Examiner* — John P Leubecker
(74) *Attorney, Agent, or Firm* — Scully, Scott, Murphy & Presser, P.C.

(57) ABSTRACT

An electronic endoscope includes a distal end portion of an insertion portion which incorporates electronic components, a metal frame which holds an observation window, an earth member which is connected to a patient-side ground of an external device, and a static-protective member which is disposed in the distal end portion to have a predetermined clearance from the metal frame and is electrically connected to the earth member to let static electricity applied to the distal end portion flow to the earth member. With the configuration, the electronic endoscope prevents occurrence of trouble, a fault, and the like in an electronic component incorporated in the distal end portion due to applied static electricity.

7 Claims, 25 Drawing Sheets

(56) References Cited

U.S. PATENT DOCUMENTS

| | | | |
|---|---|---|---|
| 4,974,075 A * | 11/1990 | Nakajima | 348/75 |
| 4,998,182 A * | 3/1991 | Krauter et al. | 361/730 |
| 5,402,769 A * | 4/1995 | Tsuji | 600/109 |
| 5,569,158 A * | 10/1996 | Suzuki et al. | 600/110 |
| 5,873,816 A * | 2/1999 | Kagawa et al. | 600/134 |
| 5,941,817 A * | 8/1999 | Crawford | 600/134 |
| 6,319,197 B1 * | 11/2001 | Tsuji et al. | 600/132 |
| 6,712,758 B1 * | 3/2004 | Campbell | 600/134 |
| 8,308,637 B2 * | 11/2012 | Ishigami et al. | 600/177 |
| 2004/0092793 A1 | 5/2004 | Akai | |
| 2008/0051634 A1 * | 2/2008 | Yamashita et al. | 600/134 |
| 2009/0036742 A1 * | 2/2009 | Watanabe | 600/178 |
| 2010/0309553 A1 * | 12/2010 | Nagamizu | 359/512 |
| 2013/0050457 A1 * | 2/2013 | Murayama et al. | 348/75 |

FOREIGN PATENT DOCUMENTS

| | | |
|---|---|---|
| JP | 2001-128937 A | 5/2001 |
| JP | 2004-148028 A | 5/2004 |
| JP | 2007-089888 A | 4/2007 |
| JP | 2009-261830 A | 11/2009 |

* cited by examiner

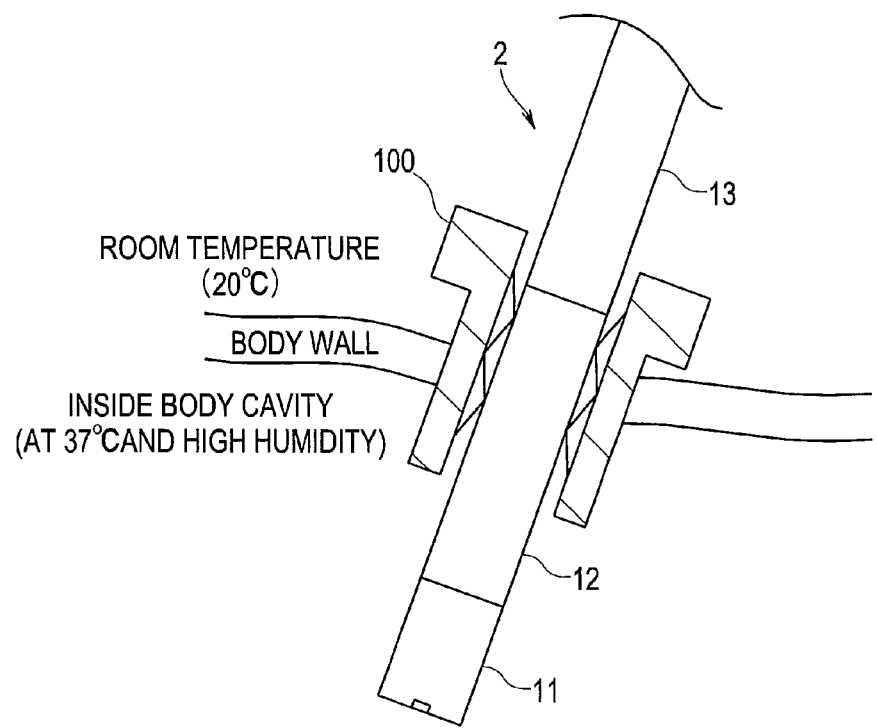
FIG.29
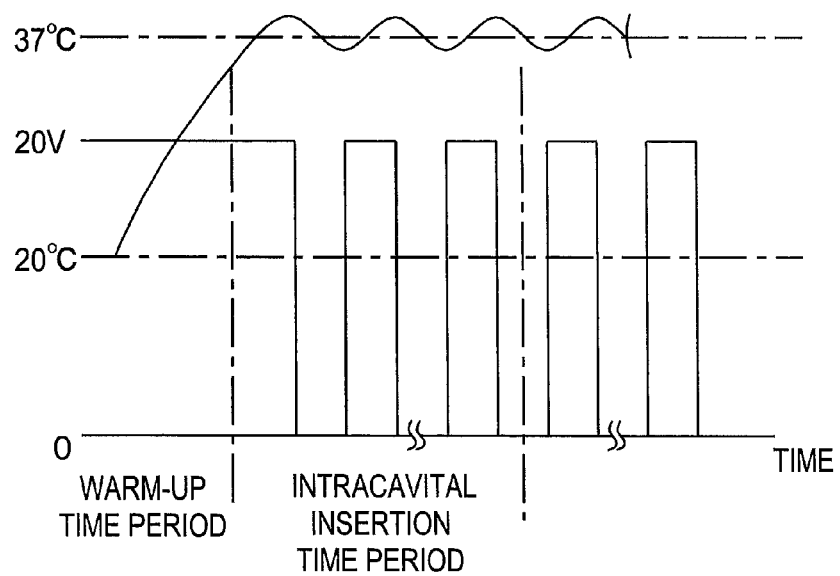

ELECTRONIC ENDOSCOPE IN WHICH STATIC-PROTECTIVE MEMBER IS PROVIDED IN DISTAL END PORTION OF INSERTION PORTION

CROSS REFERENCE TO RELATED APPLICATION

This application is a continuation application of PCT/JP2012/070655 filed on Aug. 14, 2012 and claims benefit of Japanese Application No. 2011-268189 filed in Japan on Dec. 7, 2011, the entire contents of which are incorporated herein by this reference.

BACKGROUND OF THE INVENTION

1. Field of the Invention

The present invention relates to an electronic endoscope having exposed metal at a distal end.

2. Description of the Related Art

As is well known, endoscopes are widely used for observation, treatment, and the like inside a body (inside a body cavity) of a living body or for inspection, repair, and the like in industrial plant equipment. Among endoscopes, electronic endoscopes including an image pickup apparatus with a CCD and the like placed in the image pickup apparatus have recently become mainstream. In such a conventional electronic endoscope, a holding frame made of metal which holds an optical member on a side closer to a distal end than a CCD is disposed at a distal end portion.

In the conventional electronic endoscope, fogging due to condensation may occur in an objective optical system, resulting from a temperature difference between outside air temperature and ambient temperature of an object to be examined, ambient humidity in the object to be examined, and the like. For the reason, various techniques for preventing, e.g., fogging of and condensation on an outer surface of a transparent cover member of an objective optical system have been proposed for endoscopes. For example, Japanese Patent Application Laid-Open Publication No. 2009-261830 discloses a defogging technique in an objective optical system in which an anti-fogging device which heats a thin film formed on a cover glass arranged at a distal end portion of an electronic endoscope is provided at a holding frame for the cover glass.

SUMMARY OF THE INVENTION

An electronic endoscope according to one aspect of the present invention includes a distal end portion of an insertion portion which incorporates electronic components, a metal frame which is disposed at the distal end portion and holds an observation window, an earth member which is connected to a patient-side ground of an external device, and a static-protective member which is disposed in the distal end portion to have a predetermined clearance from the metal frame and is electrically connected to the earth member to let static electricity applied to the distal end portion flow to the earth member.

BRIEF DESCRIPTION OF THE DRAWINGS

FIG. 28 is a view showing a state in which the insertion portion is inserted in a body cavity;

FIG. 29 is a graph showing a drive voltage of the anti-fogging unit, time, and temperature change;

DETAILED DESCRIPTION OF THE PREFERRED EMBODIMENT

One embodiment of the present invention will be described below with reference to the drawings.

Figure 1:
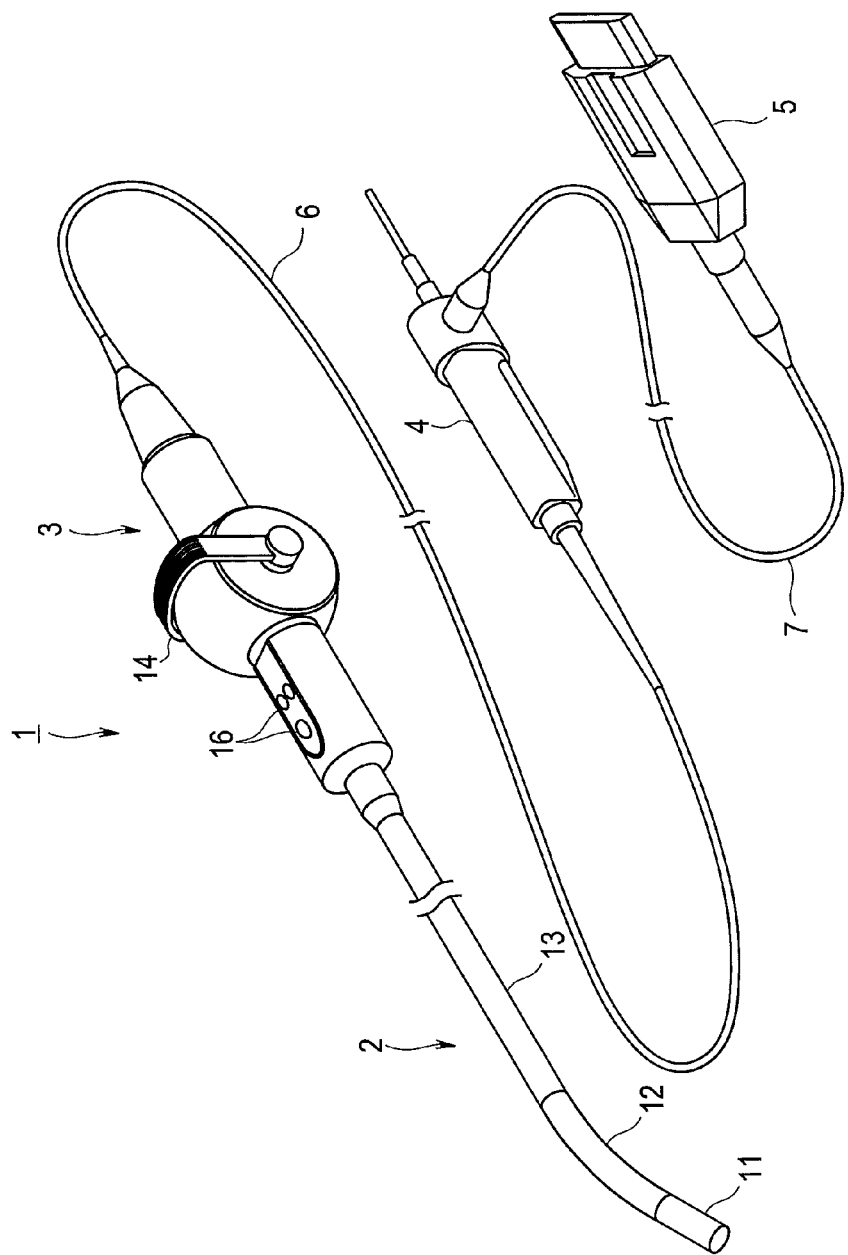
FIG. 1 is a perspective view showing an entire configuration of an endoscope apparatus.
Figure 2:
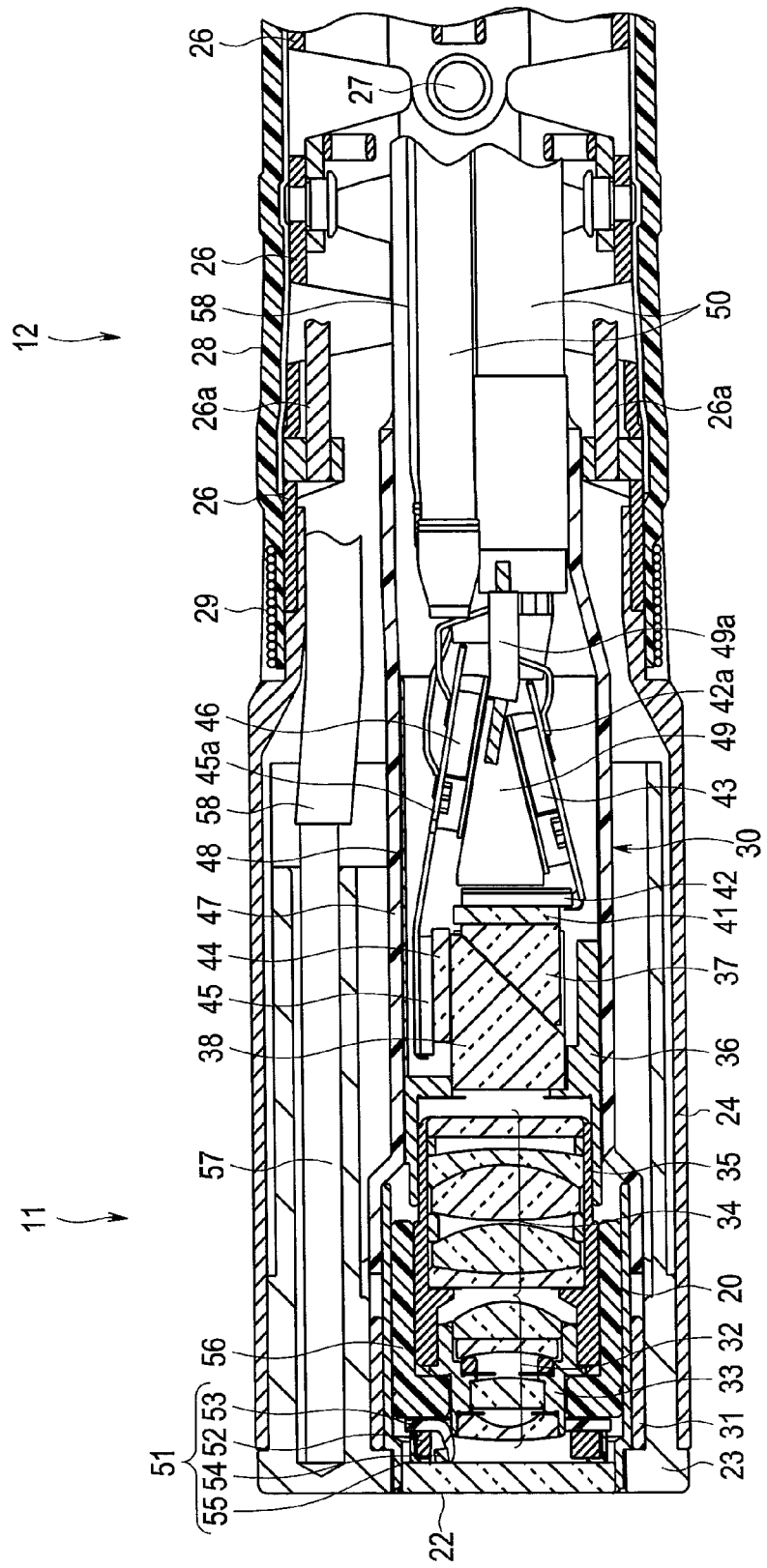
FIG. 2 is a cross-sectional view showing a configuration of a distal end part of an insertion portion.
Figure 3:
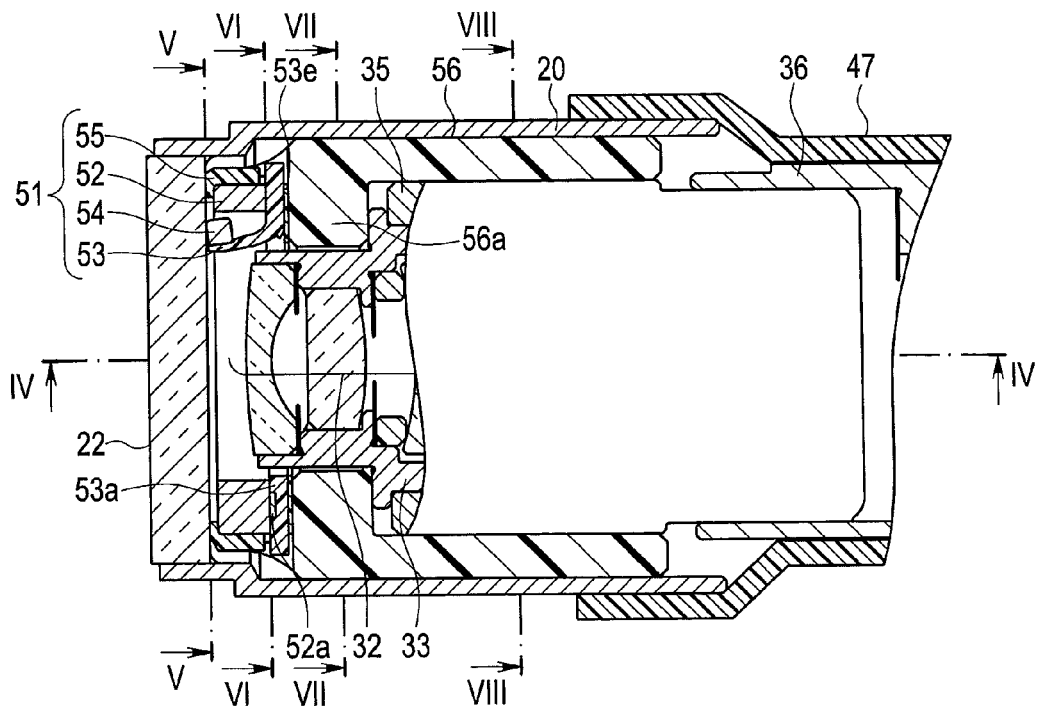
FIG. 3 is a cross-sectional view showing a configuration of a front end part of an image pickup unit.
Figure 4:
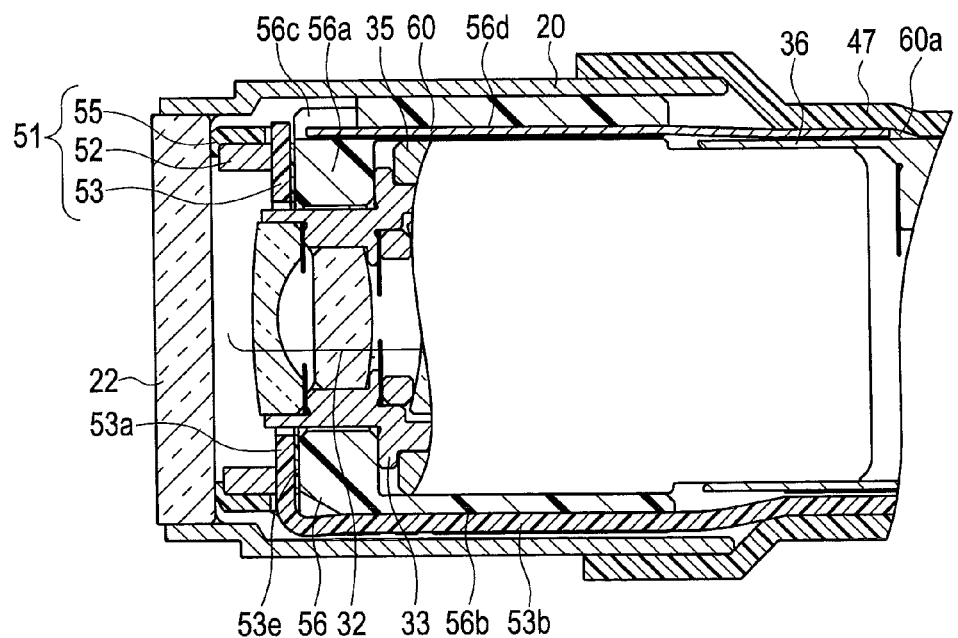
FIG. 4 is a cross-sectional view taken along line IV-IV in FIG. 3.
Figure 5:
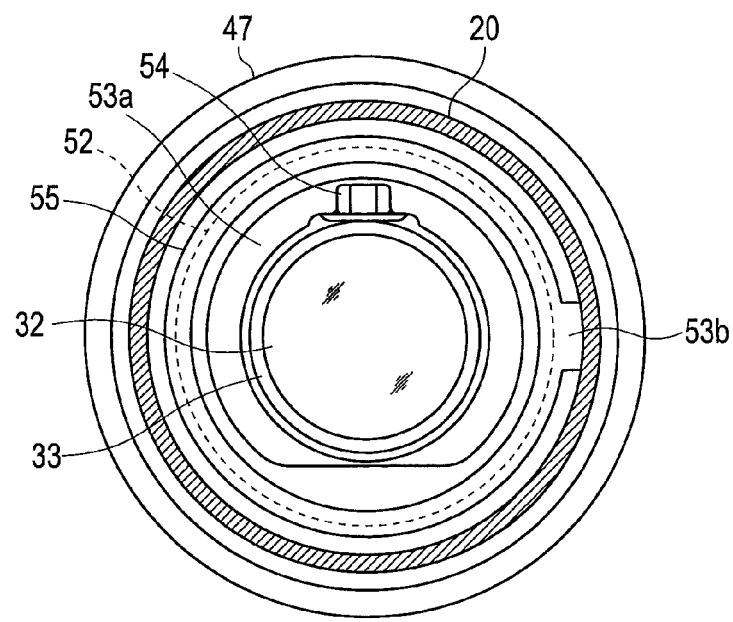
FIG. 5 is a cross-sectional view taken along line V-V in FIG. 3.
Figure 6:
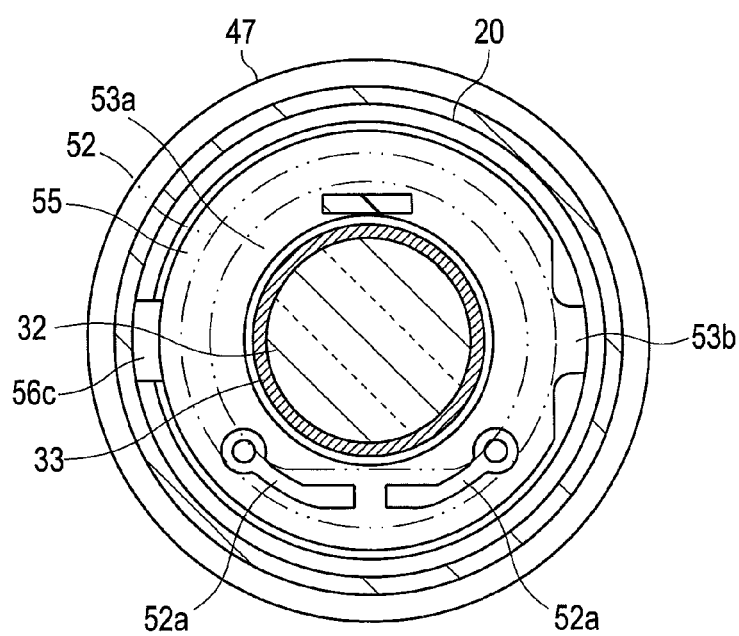
FIG. 6 is a cross-sectional view taken along line VI-VI in FIG. 3.
Figure 7:
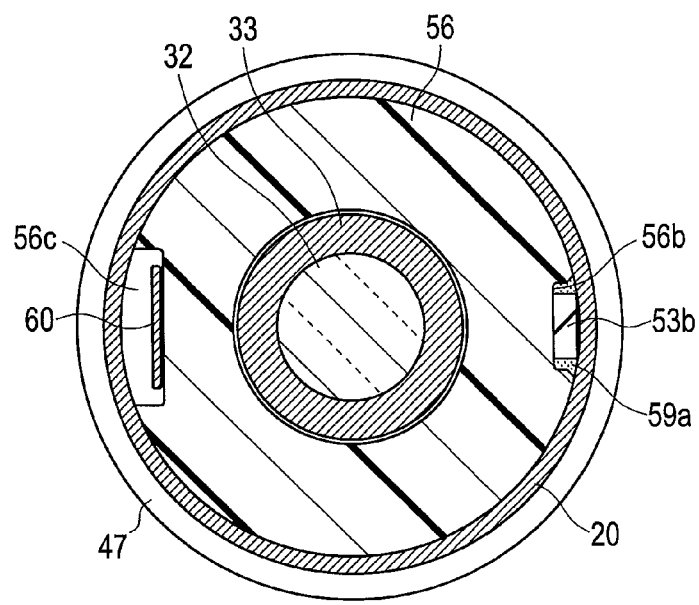
FIG. 7 is a cross-sectional view taken along line VII-VII in FIG. 3.
Figure 8:
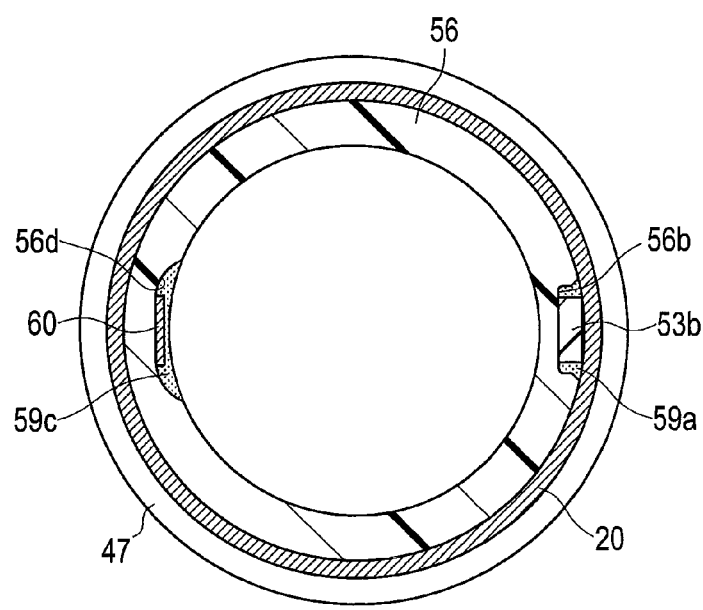
FIG. 8 is a cross-sectional view taken along line VIII-VIII in FIG. 3.
Figure 9:
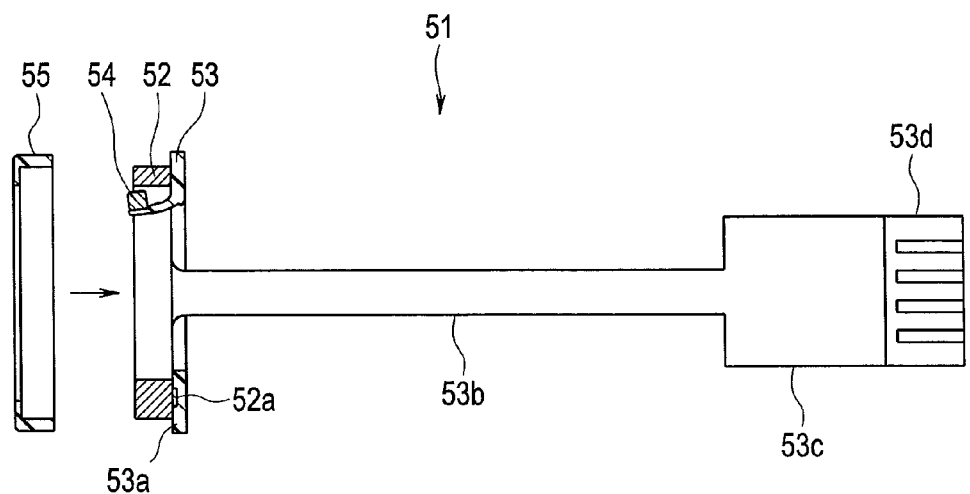
FIG. 9 is an exploded plan view showing a configuration of an anti-fogging unit.
Figure 10:
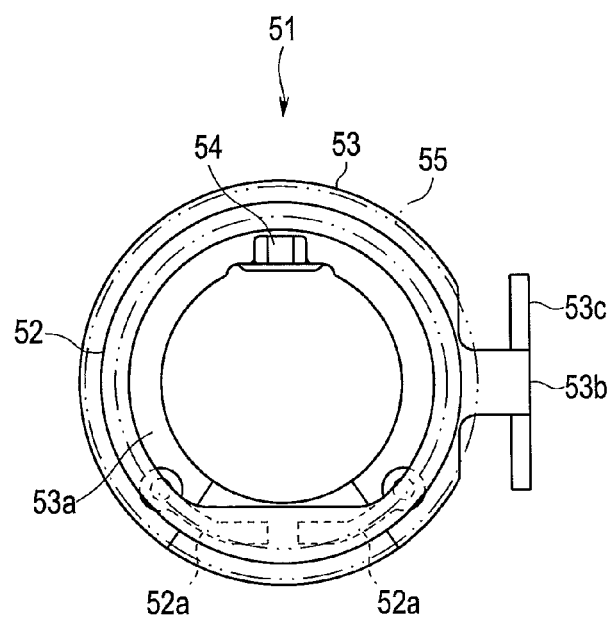
FIG. 10 is a front view showing the configuration of the anti-fogging unit.
Figure 11:
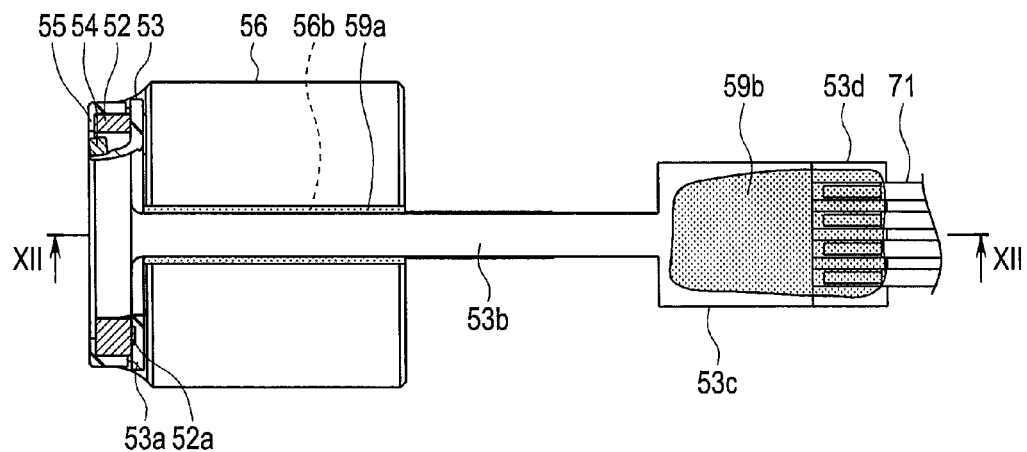
FIG. 11 is a plan view showing a configuration in which the anti-fogging unit is fastened to an insulating member for insulation and thermal insulation.
Figure 12:
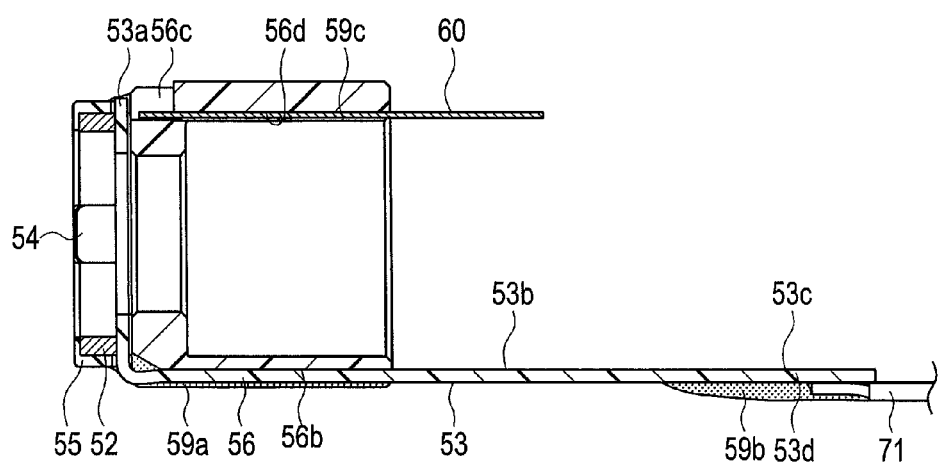
FIG. 12 is a cross-sectional view taken along line XII-XII in FIG. 11.
Figure 13:
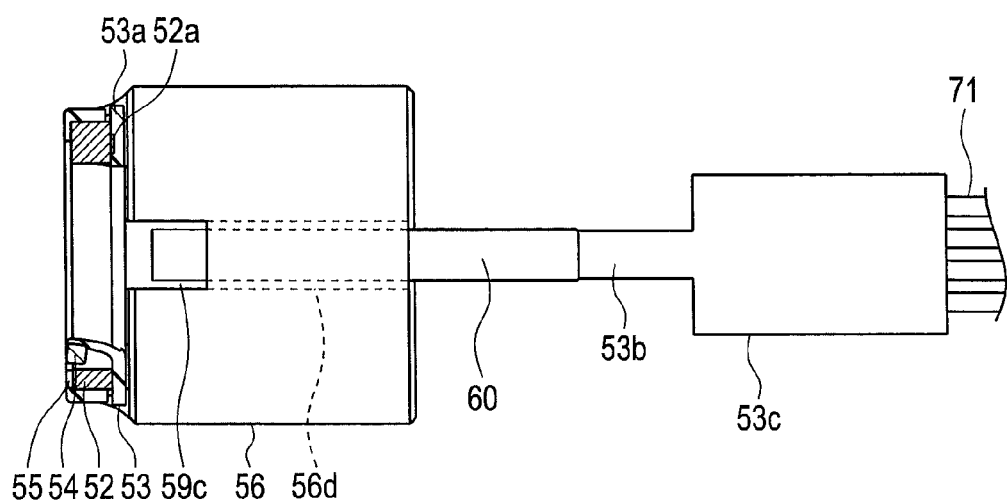
FIG. 13 is a plan view showing a configuration in which a conductive plate is fastened to the insulating member for insulation and thermal insulation.
Figure 14:
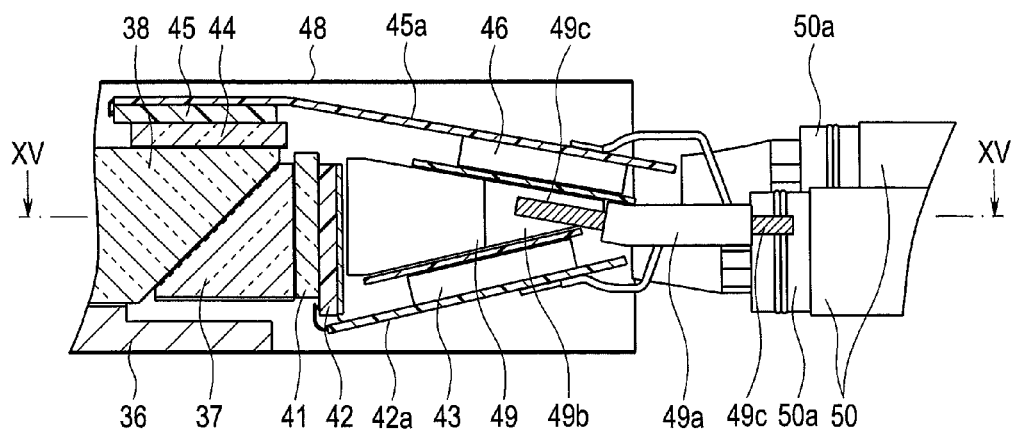
FIG. 14 is a vertical cross-sectional view showing a configuration of a part at a rear of the image pickup unit.
Figure 15:
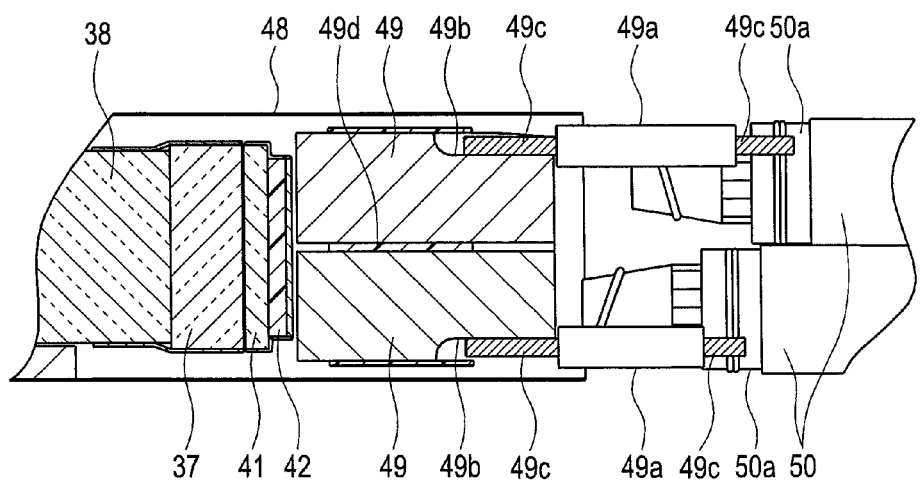
FIG. 15 is a cross-sectional view taken along line XV-XV in FIG. 14.
Figure 16:
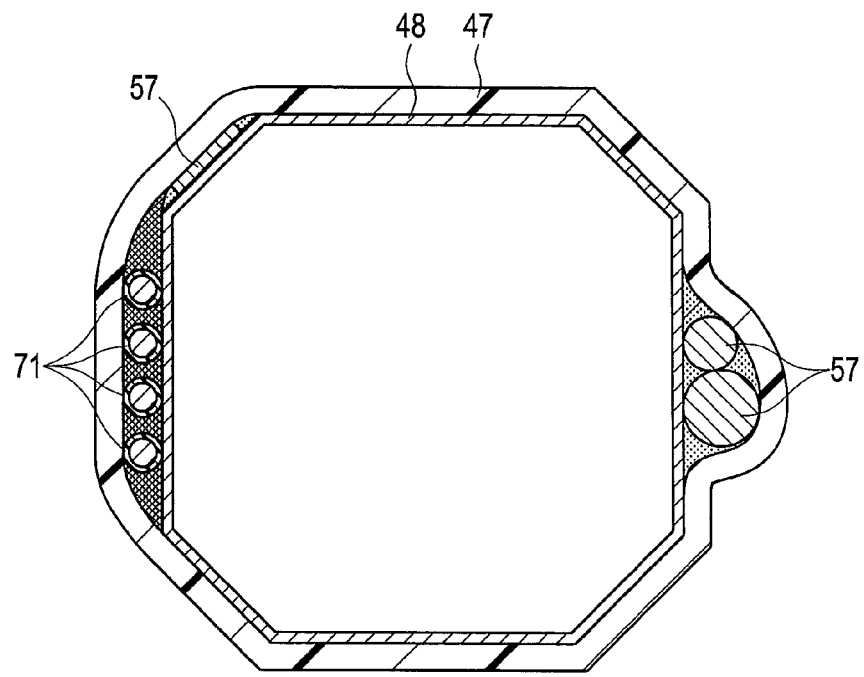
FIG. 16 is a cross-sectional view showing a layout of three radiating cables connected to a reinforcing frame.
Figure 17:
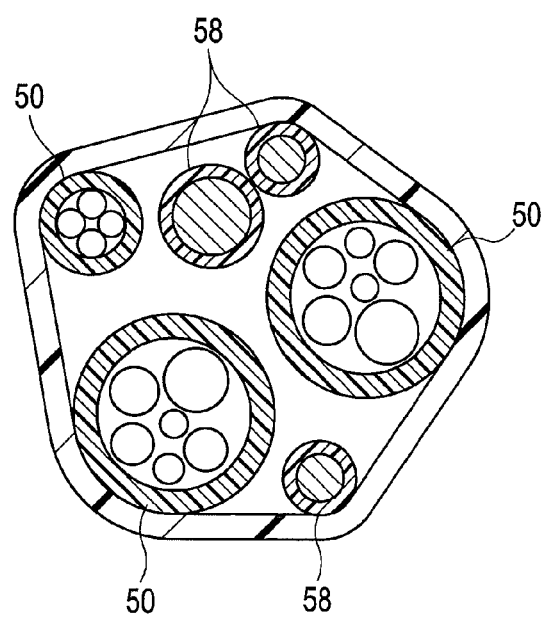
FIG. 17 is a cross-sectional view showing a part where three signal cables and the three radiating cables are coated in a heat-shrinkable tube.
Figure 18:
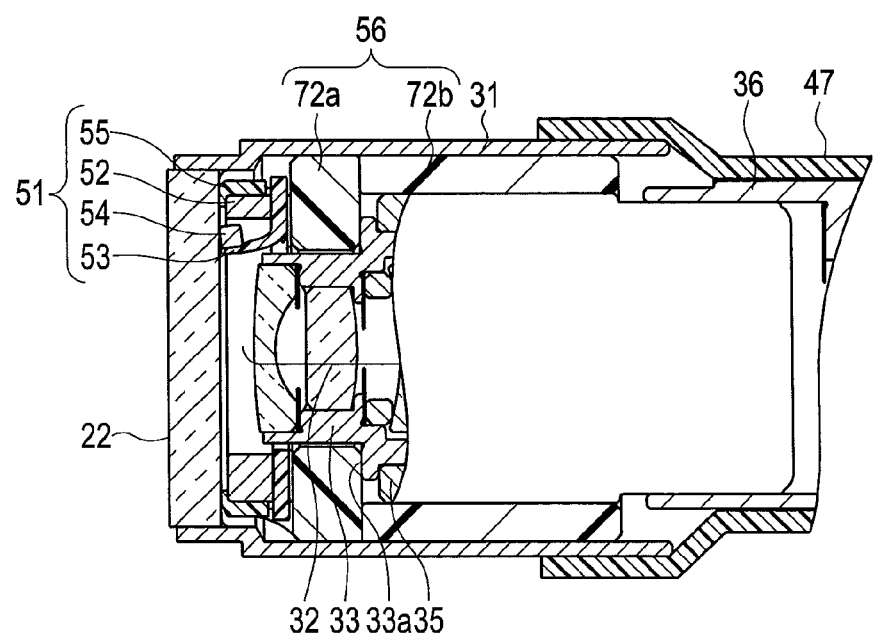
FIG. 18 is a cross-sectional view showing a first modification of the insulating member for insulation and thermal insulation.
Figure 19:
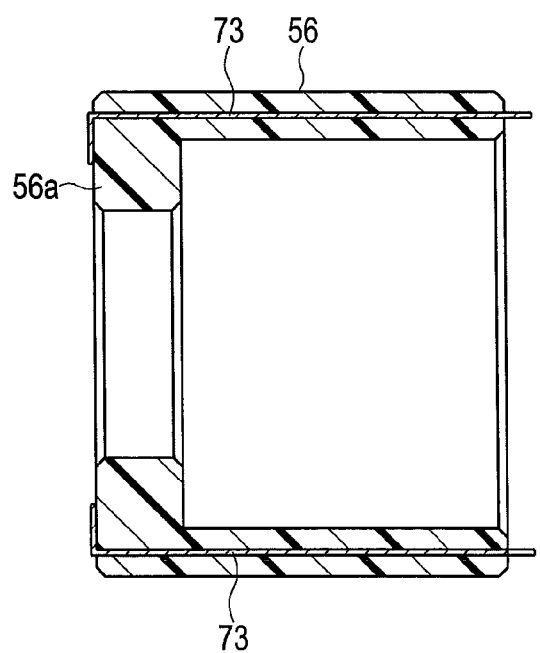
FIG. 19 is a cross-sectional view showing a second modification of the insulating member for insulation and thermal insulation.
Figure 20:
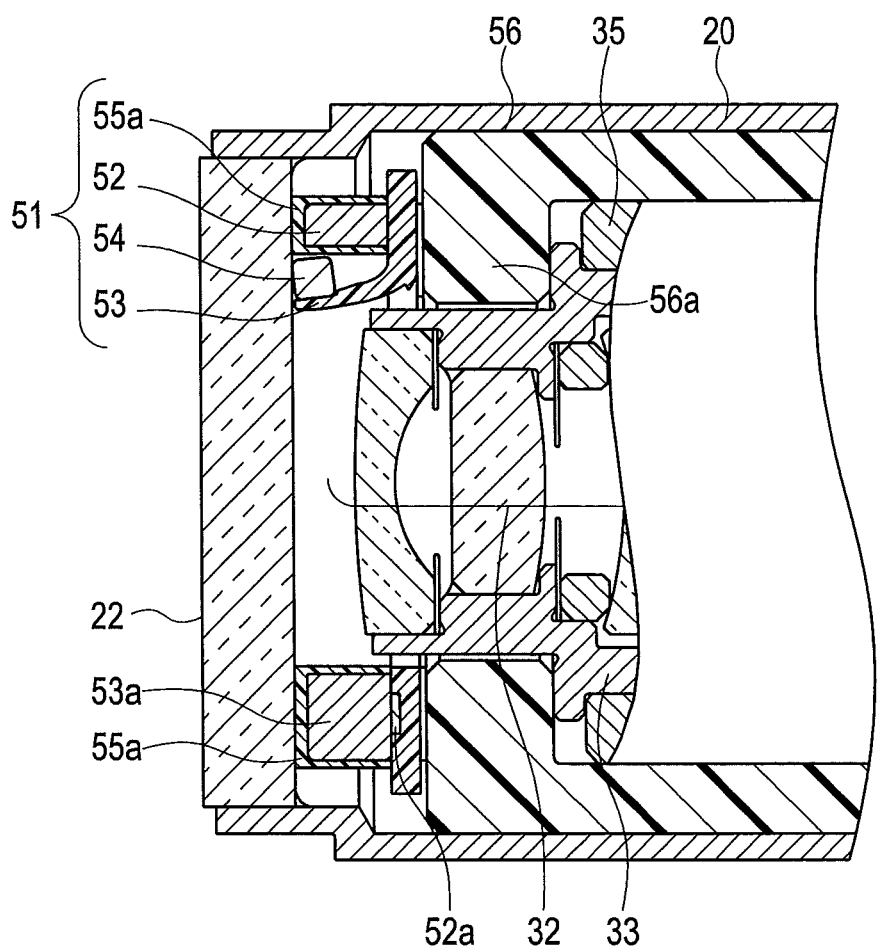
FIG. 20 is a cross-sectional view showing a first modification of the anti-fogging unit.
Figure 21:
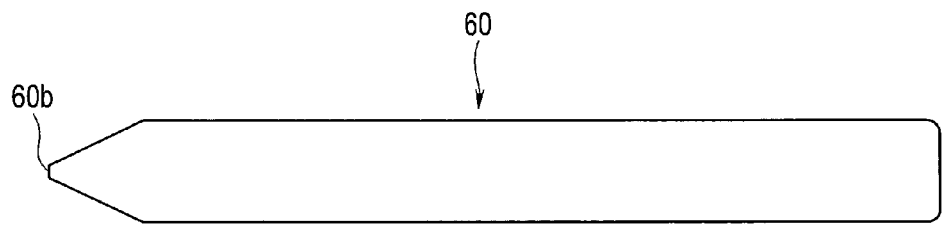
FIG. 21 is a plan view showing a first modification of a static-protective member.
Figure 22:
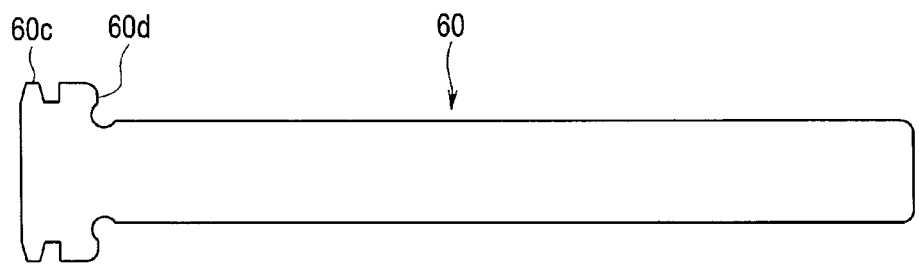
FIG. 22 is a plan view showing a second modification of the static-protective member.
Figure 23:
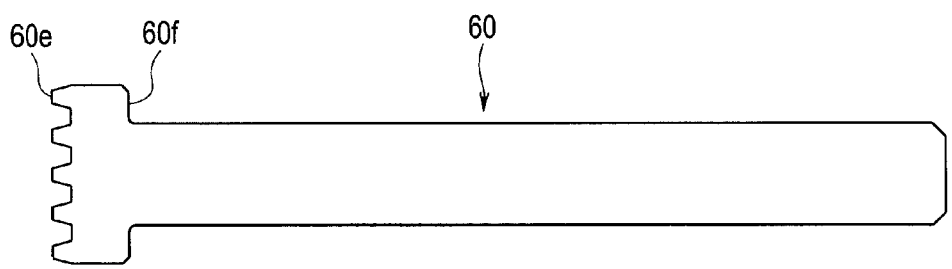
FIG. 23 is a plan view showing a third modification of the static-protective member.
Figure 24:
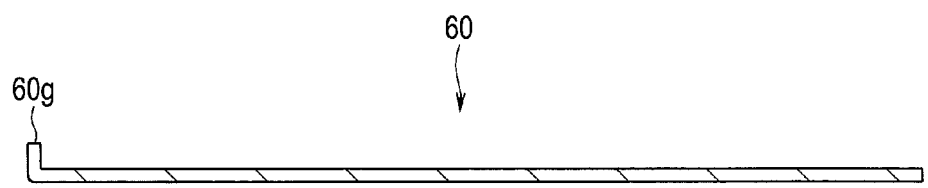
FIG. 24 is a cross-sectional view showing a fourth modification of the static-protective member.
Figure 25:
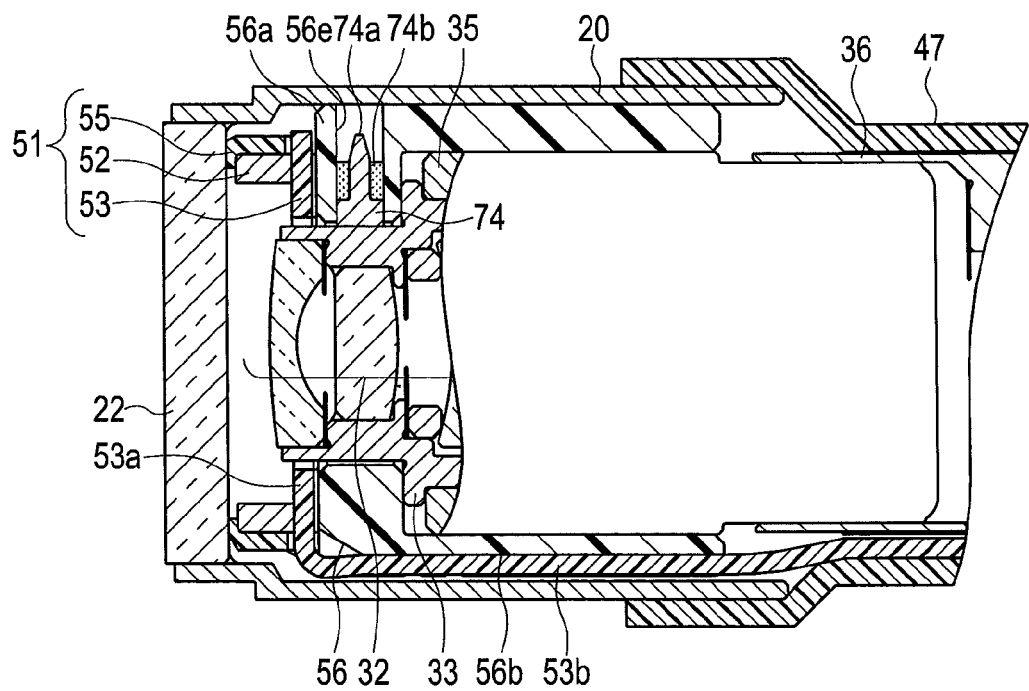
FIG. 25 is a cross-sectional view showing a fifth modification of the static-protective member.
Figure 26:
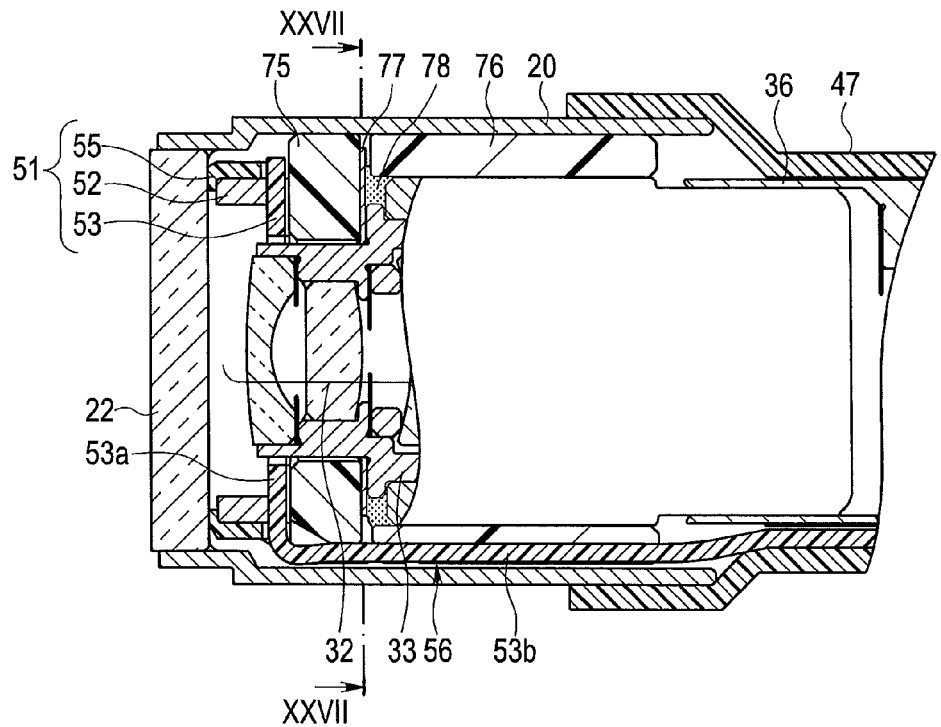
FIG. 26 is a cross-sectional view showing a sixth modification of the static-protective member.
Figure 27:
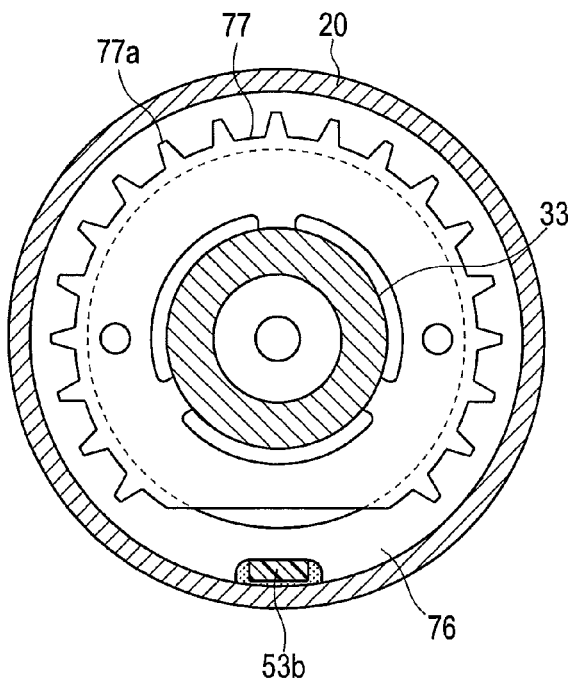
FIG. 27 is a cross-sectional view taken along line XXVII-XXVII in FIG. 26.
Figure 30:
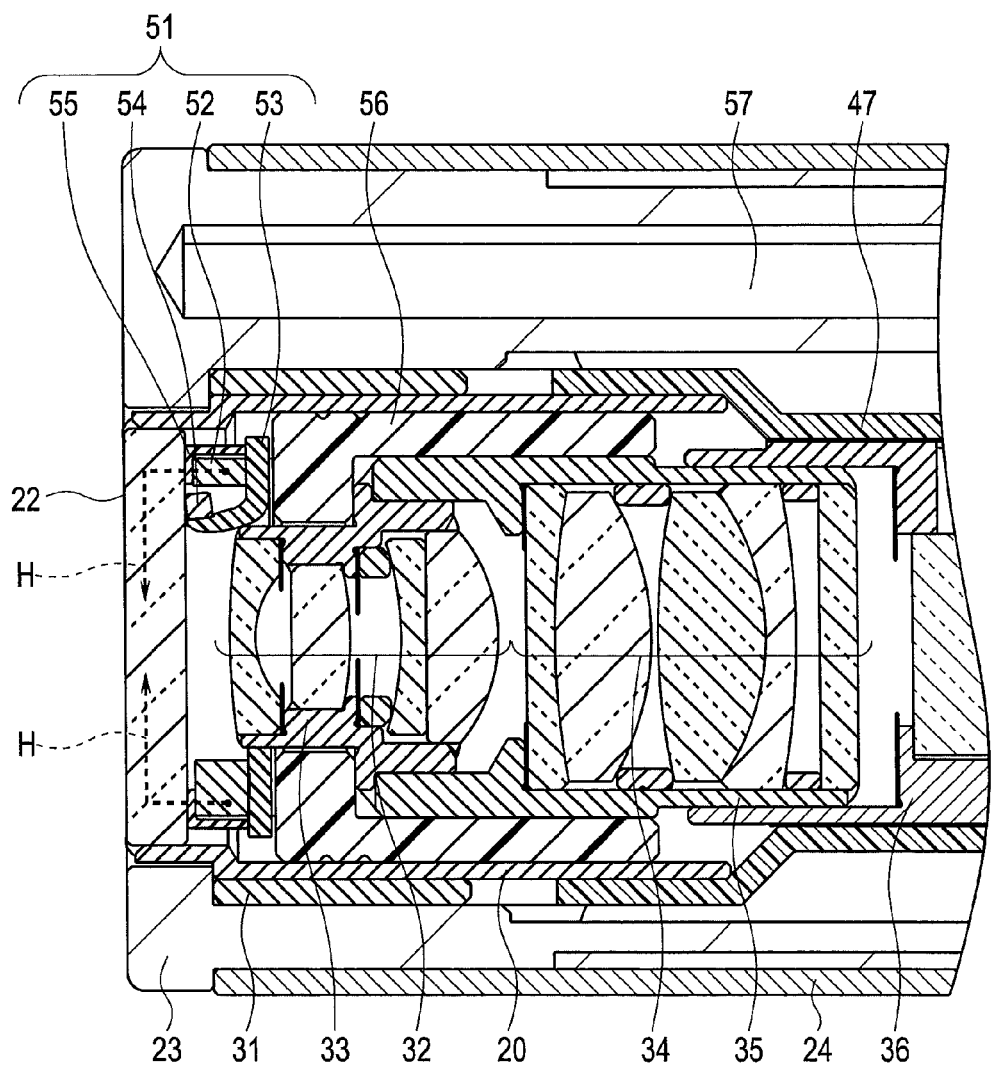
FIG. 30 is a cross-sectional view showing the distal end part of the insertion portion for explaining action of the insulating member for insulation and thermal insulation.
Figure 31:
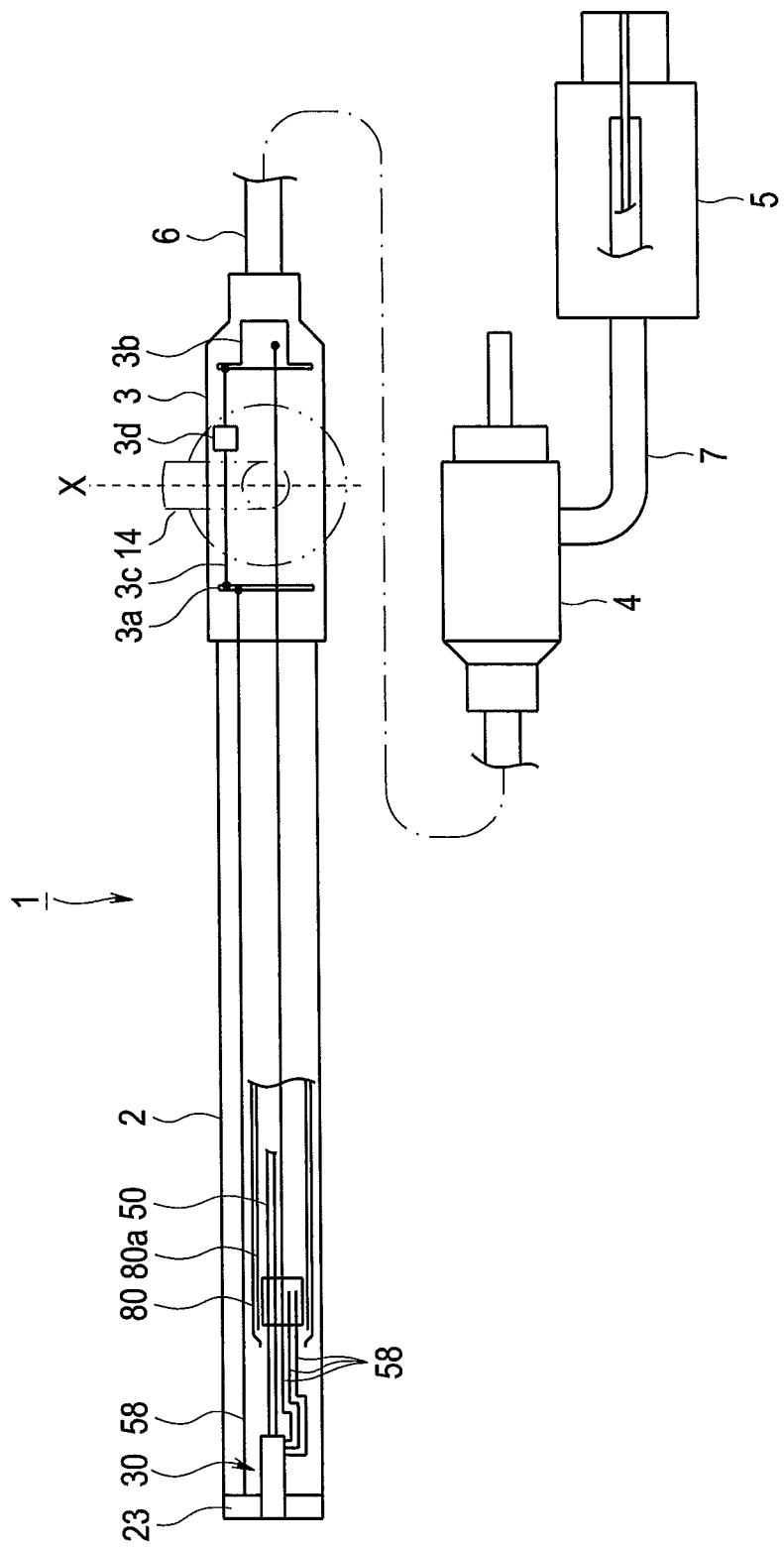
FIG. 31 is a view showing a GND system of the electronic endoscope.
Figure 32:
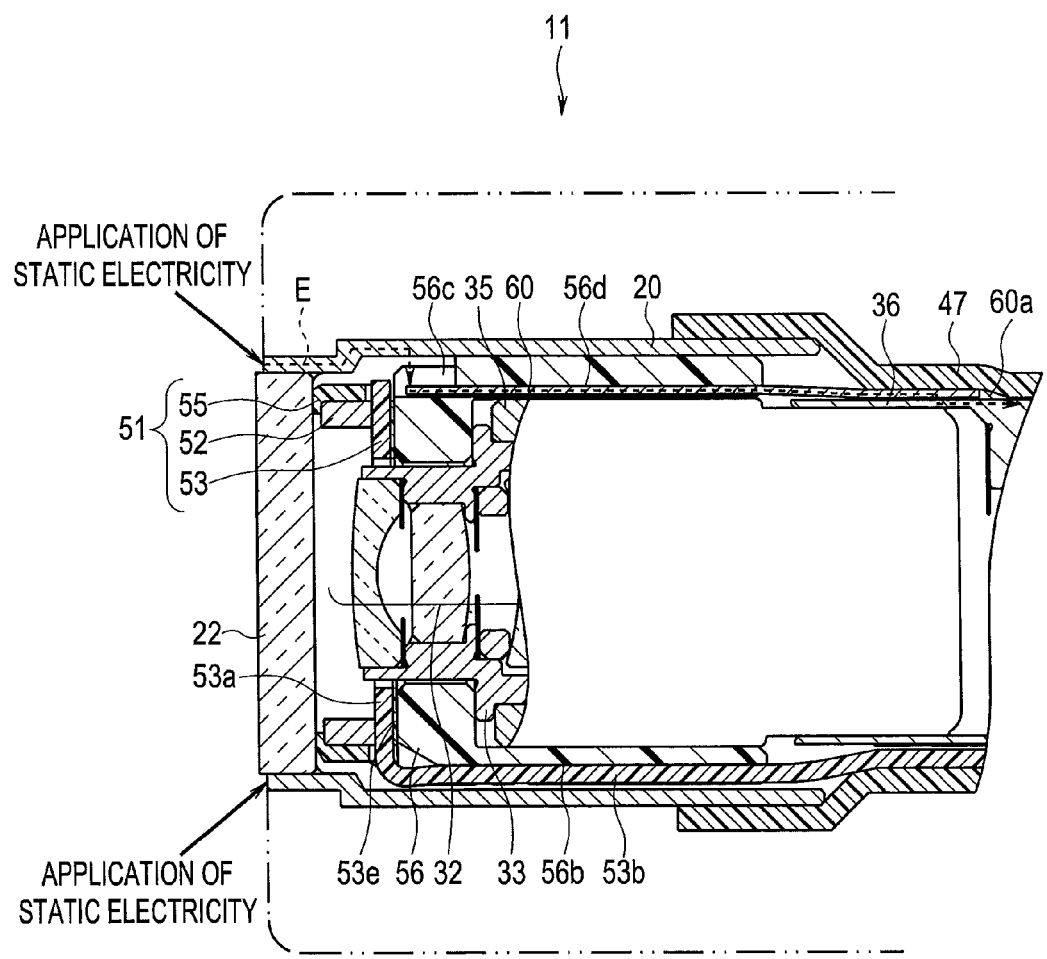
FIG. 32 is a cross-sectional view showing the distal end part of the insertion portion for explaining action of the static-protective member.

FIGS. 1 to 32 relate to the one embodiment of the present invention. FIG. 1 is a perspective view showing an entire configuration of an endoscope apparatus, FIG. 2 is a cross-sectional view showing a configuration of a distal end part of an insertion portion, FIG. 3 is a cross-sectional view showing a configuration of a front end part of an image pickup unit, FIG. 4 is a cross-sectional view taken along line IV-IV in FIG. 3, FIG. 5 is a cross-sectional view taken along line V-V in FIG. 3, FIG. 6 is a cross-sectional view taken along line VI-VI in FIG. 3, FIG. 7 is a cross-sectional view taken along line VII-VII in FIG. 3, FIG. 8 is a cross-sectional view taken along line VIII-VIII in FIG. 3, FIG. 9 is an exploded plan view showing a configuration of an anti-fogging unit, FIG. 10 is a front view showing the configuration of the anti-fogging unit, FIG. 11 is a plan view showing a configuration in which the anti-fogging unit is fastened to an insulating member for insulation and thermal insulation, FIG. 12 is a cross-sectional view taken along line XII-XII in FIG. 11, FIG. 13 is a plan view showing a configuration in which a conductive plate is fastened to the insulating member for insulation and thermal insulation, FIG. 14 is a vertical cross-sectional view showing a configuration of a part at a rear of the image pickup unit, FIG. 15 is a cross-sectional view taken along line XV-XV in FIG. 14, FIG. 16 is a cross-sectional view showing a layout of three radiating cables connected to a reinforcing frame, FIG. 17 is a cross-sectional view showing a part where three signal cables and the three radiating cables are coated in a heat-shrinkable tube, FIG. 18 is a cross-sectional view showing a first modification of the insulating member for insulation and thermal insulation, FIG. 19 is a cross-sectional view showing a second modification of the insulating member for insulation and thermal insulation, FIG. 20 is a cross-sectional view showing a first modification of the anti-fogging unit, FIG. 21 is a plan view showing a first modification of a static-protective member, FIG. 22 is a plan view showing a second modification of the static-protective member, FIG. 23 is a plan view showing a third modification of the static-protective member, FIG. 24 is a cross-sectional view showing a fourth modification of the static-protective member, FIG. 25 is a cross-sectional view showing a fifth modification of the static-protective member, FIG. 26 is a cross-sectional view showing a sixth modification of the static-protective member, FIG. 27 is a cross-sectional view taken along line XXVII-XXVII in FIG. 26, FIG. 28 is a view showing a state in which the insertion portion is inserted in a body cavity, FIG. 29 is a graph showing a drive voltage of the anti-fogging unit, time, and temperature change, FIG. 30 is a cross-sectional view showing the distal end part of the insertion portion for explaining action of the insulating member for insulation and thermal insulation, FIG. 31 is a view showing a GND system of the electronic endoscope, and FIG. 32 is a cross-sectional view showing the distal end part of the insertion portion for explaining action of the static-protective member.

As shown in FIG. 1, an electronic endoscope 1 is mainly composed of an elongated insertion portion 2, an operation portion 3 which is provided to be continuous with a proximal end of the insertion portion 2, a light guide connector 4 which is connected to a light source apparatus (not shown), and a video connector 5 which is connected to a video system center (a camera control unit: also referred to as a CCU) (not shown). Note that, in the electronic endoscope 1, the operation portion 3 and the light guide connector 4 are connected via a flexible cable (hereinafter referred to as a universal cord) 6, and the light guide connector 4 and the video connector 5 are connected via a flexible communication cable 7.

In the insertion portion 2, a distal end portion 11 which is mainly formed from a metallic member of stainless or the like, a bending portion 12, and a rigid tube 13 which is a metal tube of stainless or the like are provided to be continuous in the order from a distal end side. The insertion portion 2 is a part to be inserted into a body and incorporates cables (to be described later), a light guide bundle (not shown), and the like.

The operation portion 3 includes an angle lever 14 which remotely operates the bending portion 12 and various switches 16 for operating the light source apparatus, the video system center, and the like (all of which are not shown). The angle lever 14 is bending operation means which can operate the bending portion 12 of the insertion portion 2 in two upward and downward directions here. Note that the bending portion 12 is not limited to the two upward and downward directions and may be configured to be bendable and operable in four upward, downward, leftward, and rightward directions by providing another angle lever. Additionally, a rigid endoscope, in which a greater part of the insertion portion 2 that is the insertion portion 2 except for the bending portion 12, is illustrated here as the electronic endoscope 1. The electronic endoscope 1, however, is not limited to a rigid endoscope, and a flexible endoscope whose insertion portion 2 has flexibility may be used instead.

An internal configuration of a distal end of the insertion portion 2 in the electronic endoscope 1 will be described in detail with reference to FIG. 2.

As shown in FIG. 2, the distal end portion 11 of the insertion portion 2 has a distal end rigid portion 23 made of metal. An image pickup unit 30 penetrates through and is inserted in the distal end rigid portion 23 and is fixed to the distal end rigid portion 23. The distal end rigid portion 23 fits in a sheathed tube 24 made of metal, and the sheathed tube 24 is fixed by, for example, a fixation pin (not shown).

A proximal end of the sheathed tube 24 is coupled to a bending piece 26 which is disposed in the bending portion 12. A plurality of bending pieces 26 are disposed in the bending portion 12. Adjacent ones of the bending pieces 26 are coupled by a pivot rivet 27 so as to be pivotable. The bending pieces 26 each pivot about the pivot rivet 27 when two bending operation wires 26a which are disposed at a top and at a bottom are pulled and relaxed, respectively, by operation of the angle lever 14. With the configuration, the bending portion 12 is bent and operated in the two upward and downward directions here. Note that the bending portion 12 has a flexible tube 28 which is formed of, e.g., fluoro rubber so as to integrally cover outer circumferences of the plurality of bending pieces 26. A distal end outer circumferential portion of the flexible tube 28 is connected to the proximal end of the sheathed tube 24 by a thread-wound adhesive portion 29. Note that a radiating cable 58 into which a metallic radiating wire 57 is engageably inserted and to which the radiating wire 57 is fastened is connected to the distal end rigid portion 23. The radiating cable 58 is provided to extend rearward and is intended to release heat of the distal end rigid portion 23 rearward.

A transparent cover member 22 which is an optical member (objective optical system) provided at a distal end of the image pickup unit 30 and serving as an observation window fits with and is held by an observation window holding frame 20 made of metal which is formed in a substantially ring shape. The observation window holding frame 20 constitutes a first metal frame here and fits to be inserted in the distal end rigid portion 23 and is fixed to the distal end rigid portion 23. A ring-like spacer 31 which fits on the observation window holding frame 20 is provided on an outer circumferential side of the observation window holding frame 20 behind the transparent cover member 22 in order for the image pickup unit 30 to fit in and be fixed to the distal end rigid portion 23. Note that a member made of non-metal and in a substantially ring shape which is formed of plastic resin, ceramic, or the like is adopted as the spacer 31 for the purpose of not transferring heat generated by driving of the image pickup unit 30 to a distal end (member) of the endoscope.

The image pickup unit 30 according to the present embodiment has a well-known configuration and has a first lens holding frame 33 made of metal which holds a first group 32 of objective lenses serving as an objective optical system, a second lens holding frame 35 which holds a second group 34 of objective lenses serving as an objective optical system, and a unit holding frame 36 made of metal which holds an image sensor and the like. Note that an insulating frame 56 which is an insulating member formed of a material lower in thermal conductivity than metal is provided between the first lens holding frame 33 and the observation window holding frame 20. The first lens holding frame 33 fits in and is fixed to the second lens holding frame 35. The second lens holding frame 35 fits in and is fixed to the unit holding frame 36. Note that the first lens holding frame 33 and second lens holding frame 35 constitute a second metal frame here and that the unit holding frame 36 made of metal constitutes a third metal frame here.

The image sensor and the like held by the unit holding frame 36 according to the present embodiment include two solid image pickup devices (hereinafter simply referred to as image pickup devices) 42 and 45, such as a CCD and a CMOS, which detect photographing light condensed by the individual groups 32 and 34 of objective lenses and split by two prisms 37 and 38. Note that a reinforcing frame 48 made of metal which serves both as a radiator plate and an earth member (a member to be connected to a patient-side GND) is present behind the unit holding frame 36 so as to cover the individual prisms 37 and 38, the individual image pickup devices 42 and 45, and the individual image pickup drive circuits 43 and 46 and is joined to the unit holding frame 36 so as to be electrically continuous with the unit holding frame 36. Note that three radiating cables 58 (to be described later) are also connected to the reinforcing frame 48 to escape heat, generated by driving of the solid image pickup devices, rearward. Parts which are made to fit with each other of each adjacent two of the first lens holding frame 33, the second lens holding frame 35, the unit holding frame 36, and the reinforcing frame 48 that are made of metal are fastened with adhesive.

The first image pickup device 42 is joined to one surface of the prism 37 located behind the image pickup device 42 via a cover glass 41. The second image pickup device 45 is joined to one surface of the prism 38 located in front of the image pickup device 45 via a cover glass 44. Surfaces of the two prisms 37 and 38 according to the present embodiment are bonded together, and a reflecting surface is formed so as to reflect, for example, only light in a predetermined wavelength band of visible light. By way of example, the two prisms 37 and 38 are set such that only G (green) light is refracted by the reflecting surface, such that B (blue) light and R (red) light are guided to the first image pickup device 42, and such that G (green) light is guided to the second image pickup device 45.

The image pickup devices 42 and 45 are each configured here to individually perform image processing and are electrically connected to the two image pickup drive circuits 43 and 46 constituting a portion of an electronic image pickup circuit via FPCs 42a and 45a (see FIG. 14). The image pickup drive circuits 43 and 46 are individually connected to signal cables 50 which are inserted in and extend through the insertion portion 2, the operation portion 3, and the light guide connector 4 and are provided to extend to the video connector 5. Two heat sinks 49 which can be connected with solder and are blocks made of copper are interposed between the two image pickup drive circuits 43 and 46. As will be described in detail later, the two heat sinks 49 are electrically connected to overall shielding members 50a, respectively, of the signal cables 50 by jumper wires 49a.

Note that the individual prisms 37 and 38, the individual image pickup devices 42 and 45, and the individual image pickup drive circuits 43 and 46 that are held by the unit holding frame 36 are covered with non-conductive adhesive, a filling agent, or the like, and the reinforcing frame 48 is coated in a heat-shrinkable tube 47 around the reinforcing frame 48. The heat-shrinkable tube 47 integrally coats a part from an outer circumferential part of a proximal end of the observation window holding frame 20 to outer circumferential parts of distal ends of the signal cables 50, the radiating cables 58, and the like. As described above, the observation window holding frame 20 that holds the transparent cover member 22 and is closed on a distal end side and the spacer 31 fit with each other. Since the part from the outer circumferential portion of the proximal end of the observation window holding frame 20 to the outer circumferences of the distal ends of the signal cables 50, the radiating cables 58, and the like is coated in the heat-shrinkable tube 47, the image pickup unit 30 is in a hermetically held state in the distal end portion 11.

As shown in FIGS. 3 and 4, an insulating frame 56 is formed of, for example, PEEK (polyetheretherketone) resin with low water absorption which is one of super engineering plastics or ceramic that is a sintered member in order to prevent fogging inside an objective lens due to moisture permeating the objective lens and is a substantially cylindrical member for insulation and thermal insulation which has, on a front side, a rib 56a which is formed to extend in an inner diameter direction. The insulating frame 56 is arranged to fit in the observation window holding frame 20 and fit on the first lens holding frame 33 and the second lens holding frame 35 in order to space the observation window holding frame 20 apart from the first and second lens holding frames 33 and 35 by predetermined distances. Note that, in order to prevent entry of moisture into and air paths in the observation window holding frame 20, adhesive is applied to an outer circumferential face and an inner circumferential face of the insulating frame 56 and that the insulating frame 56 is fixed while the insulating frame 56 fits with and is in surface contact with the observation window holding frame 20, the first lens holding frame 33, and the second lens holding frame 35.

More specifically, the insulating frame 56 is fitted on the first lens holding frame 33 and the second lens holding frame 35 while a small-diameter portion on the front side provided with the rib 56a of the inner circumferential face is glued in surface contact with a front portion of an outer circumferential face of the first lens holding frame 33, and a large-diameter portion on a rear side of the inner circumferential face is glued in surface contact with an outer circumferential face of the second lens holding frame 35 that is made to fit with a rear part of the first lens holding frame 33. Additionally, the insulating frame 56 is arranged while the outer circumferential face is glued in surface contact with an inner circumferential face of the observation window holding frame 20. With the configuration, the insulating frame 56 is made to fit with the observation window holding frame 20, the first lens holding frame 33, and the second lens holding frame 35 while entry of moisture into and air paths in the observation window holding frame 20 are prevented.

In the above-described manner, the observation window holding frame 20 and the first and second lens holding frames 33 and 35 are arranged to be not in contact with and be spaced apart by the predetermined distances from each other, with the insulating frame 56 between the observation window holding frame 20 and the first and second lens holding frames 33 and 35. Note that the insulating frame 56 also constitutes a member for aligning an axis of the observation window holding frame 20 with axes of the first lens holding frame 33 and the second lens holding frame 35.

As shown in FIGS. 3 to 12, the insulating frame 56 is provided with an anti-fogging unit 51 which prevents, e.g., fogging of and condensation on the transparent cover member 22 serving as the observation window, the first group 32 of objective lenses (in particular, a surface of a most distal end lens), and the like. The anti-fogging unit 51 has an anti-fogging device 52 which serves as an electronic member, an FPC 53 which is fastened to the insulating frame 56, a thermistor 54 for temperature sensing which is provided on the FPC 53, and a device-insulating frame 55 of an insulator which is interposed between the anti-fogging device 52 and the transparent cover member 22 and insulates the observation window holding frame 20 and the anti-fogging device 52 from each other.

The anti-fogging device 52 has a substantially ring shape, is glued to one surface of a ring portion 53a on a front side of the FPC 53, and is arranged while being welded by soldering or the like to two contact lands 52a which are formed at one surface of the FPC 53. That is, the anti-fogging device 52 is in contact with and is electrically connected to the two contact lands 52a. The anti-fogging device 52 provided on the ring portion 53a is covered from a front side by the ring-shaped device-insulating frame 55 that is formed of heat-resistant resin, such as sulphone-based resin (see FIG. 9). The device-insulating frame 55 ensures insulation by keeping the anti-fogging device 52 out of contact with the observation window holding frame 20 made of metal and is provided so as to cover an outer side surface and a front end face of the anti-fogging device 52 in order to prevent static electricity applied via the observation window holding frame 20 from falling on the anti-fogging device 52. The device-insulating frame 55 is installed in contact with a back surface of the transparent cover member 22 serving as the observation window and transmits heat of the anti-fogging device 52 to the transparent cover member 22.

The thermistor 54 is mounted on a protruding piece which is curved forward from an inner side of the ring portion 53a (see FIGS. 5, 9, and 10). The thermistor 54 is arranged in contact with the back surface of the transparent cover member 22 serving as the observation window. The FPC 53 also has an elongated wiring film portion 53b which is provided to be curved rearward and extend from a portion of an outer circumference of the ring portion 53a and a rectangular wiring connection portion 53c which is integrally formed at a rear end portion of the wiring film portion 53b (see FIGS. 9 and 10).

In the wiring film portion 53b, a plurality of pieces of wiring (not shown) which are electrically connected to the anti-fogging device 52 and the thermistor 54 are printed in an insulated state. The wiring film portion 53b is arranged in a recessed FPC installation groove 56b which is formed in an outer circumferential portion of the insulating frame 56 in a longitudinal direction (see FIGS. 7 and 8), an adhesive 59a is deposited in a gap left in the FPC installation groove 56b in order to prevent entry of moisture into and air paths in the observation window holding frame 20, and the wiring film portion 53b is fastened to the insulating frame 56 (see FIGS. 7, 8, 11, and 12). Note that the insulating frame 56 here has the FPC installation groove 56b in the outer circumferential portion and is thus configured such that the wiring film portion 53b can be easily fixed to the FPC installation groove 56b with the adhesive 59a at the time of assembly of the FPC 53. That is, when the wiring film portion 53b is fixed to the FPC installation groove 56b, in which the wiring film portion 53b is installed, the adhesive 59a for preventing entry of moisture into and air paths in the observation window holding frame 20 at the time of making the insulating frame 56 and the observation window holding frame 20 fit with each other can be easily filled. In the FPC 53, a rear surface of the ring portion 53a and a front end face of the rib 56a of the insulating frame 56 are glued with a two-sided sticky member 53e, such as polyimide tape.

The wiring connection portion 53c is provided with an electric contact portion 53d which is provided with a plurality of connection lands for electrical connection with the anti-fogging device 52 and the thermistor 54. Element wires of four pieces 71 of wiring are individually soldered to the plurality of connection lands of the electric contact portion 53d (see FIGS. 11 and 12). Note that an insulating resin 59b is deposited on the electric contact portion 53d, to which the four pieces 71 of wiring are connected (see FIGS. 11 and 12).

In the insulating frame 56, a recessed notched portion 56c is formed in a distal end part of a part on a side opposite from the FPC installation groove 56b, in which the wiring film portion 53b is installed, of the outer circumferential portion such that a portion of an outer circumference is not in contact with an inner circumferential face of the observation window holding frame 20 (see FIGS. 4 and 12). That is, a space is formed at a part of an outer circumferential portion of a distal end between the insulating frame 56 and the observation window holding frame 20 by the notched portion 56c while the insulating frame 56 fits in the observation window holding frame 20 (see FIG. 4). In the insulating frame 56, a recessed static-protective member installation groove 56d, in which a conductive plate 60 serving as a static-protective member is installed, is formed on an inner circumferential face side to extend rearward from the notched portion 56c. The static-protective member installation groove 56d penetrates through the rib 56a of the insulating frame 56 and communicates with the notched portion 56c (see FIGS. 4, 12, and 13).

As shown in FIG. 13, the conductive plate 60 arranged in the static-protective member installation groove 56d is a metal flat plate which has two corner portions (pointed edge portions) in a shape of a pointed end at least on a front side and whose plate surface is substantially elongated rectangular, penetrates through and is inserted in the rib 56a of the insulating frame 56, and is arranged such that a front part is located in the notched portion 56c. The conductive plate 60 is also fastened to the insulating frame 56 by depositing an adhesive 59c in a gap left in the static-protective member installation groove 56d in order to prevent entry of moisture into and air paths in the observation window holding frame 20 (see FIGS. 8 and 12). Note that a rear end part of the conductive plate 60 is joined to an outer circumferential portion of a distal end of the unit holding frame 36 made of metal by connection using solder 60a and is electrically connected to the unit holding frame 36 (see FIG. 4). The conductive plate 60 is glued and fixed such that a surface has a clearance of about 0.2 mm from the inner circumferential face of the observation window holding frame 20 in the notched portion 56c of the insulating frame 56. With the configuration, insulation can be ensured between the distal end of the endoscope and the conductive plate 60. Although a leakage current during use of a radio knife does not flow, a current flows to the conductive plate 60 side only at a high voltage such as static electricity. For the reason, a current does not flow to an electronic component side, and occurrence of problems can be prevented.

Note that the insulating frame 56 is installed such that the conductive plate 60 does not protrude from the inner circumferential face by providing the recessed static-protective member installation groove 56d in an inner circumferential portion. With the configuration, the second lens holding frame 35 that fits in the insulating frame 56 can freely rotate about a central axis in the longitudinal direction in the insulating frame 56 and can easily perform deflection angle rotation adjustment of each of the groups 32 and 34 of objective lenses.

As shown in FIGS. 14 and 15, recessed portions 49b, to which core wires 49c of the jumper wires 49a are soldered, are formed in rear portions of side surfaces on sides opposite from respective surfaces, of the above-described two blocky heat sinks 49 disposed between the individual image pickup drive circuits 43 and 46, at which the heat sinks 49 are joined. The formation of the recessed portions 49b allows prevention of bulging of outer shapes of connection portions between the two heat sinks 49 and the jumper wires 49a. Note that surfaces of the recessed portions 49b are provided with surface treatment for solder connection. The two heat sinks 49 are joined with an insulating member 49d, such as insulating tape, between the heat sinks 49, and electrical insulation between the heat sinks 49 is kept. Since the two heat sinks 49 are individually connected to the jumper wires 49a, the two heat sinks 49 are not electrically like a loop antenna, and the insulating member 49d can reduce noise generated from the solid image pickup devices.

Note that the two heat sinks 49 also serve as holding members which hold the respective image pickup drive circuits 43 and 46 that are CCD (CMOS) drivers and absorb heat of the respective image pickup drive circuits 43 and 46 that generate large amounts of heat. Heat of the two heat sinks 49 are transferred to the overall shielding members 50a of the signal cables 50 via the jumper wires 49a and are escaped rearward.

As shown in FIG. 16, in the reinforcing frame 48 serving both as the radiator plate and the earth member, the round radiating wires 57 of two radiating cables 58 are connected with solder to one surface, and the flat radiating wire 57 of one radiating cable 58 is connected with solder to an inclined surface portion on one side which is formed at a corner portion remote from the one surface, to which the radiating wires 57 are connected. Note that at least one of the three radiating cables 58 also serves as the earth member (GND cable) and is connected to the patient ground (GND). The three radiating cables 58 are arranged together with the three signal cables 50 in the heat-shrinkable tube 47 such that the three radiating cables 58 are separated into two and one behind the reinforcing frame 48. As described above, since the three radiating cables 58 are arranged to be separated into two and one behind the reinforcing frame 48 in the heat-shrinkable tube 47, heat absorbed by the reinforcing frame 48 does not concentrate and is efficiently radiated by the three radiating cables 58, and increase in temperature of the image pickup unit 30 is prevented. Note that two of the three signal cables 50 in FIG. 17 are connected to an image pickup system, the remaining one is connected to the anti-fogging unit, and that the signal cables 50 are intended to transmit and receive various signals and supply power.

The individual radiating wires 57 in the three radiating cables 58 are connected with solder in neighborhoods of the individual image pickup drive circuits 43 and 46 that generate large amounts of heat in the reinforcing frame 48. It is thus possible to provide the image pickup unit which has reduced noise by efficiently absorbing and radiating heat around the individual image pickup drive circuits 43 and 46, whose temperatures are highest.

(First Modification of Insulating Member)

As shown in FIG. 18, the insulating frame 56 for insulation and thermal insulation may be constructed by combining two members which are identical in outer diameter, a ring-shaped insulating ring 72a which is arranged on the front side and a tubular insulating tube 72b which is arranged on the rear side.

More specifically, the insulating frame 56 has the insulating ring 72a that is glued in surface contact with a front flange 33a of the first lens holding frame 33 and the insulating tube 72b that is glued in surface contact with the outer circumferential face of the second lens holding frame 35, and a rear end face of the insulating ring 72a and a front end face of the insulating tube 72b are in surface contact and are glued and fixed with adhesive. That is, the insulating frame 56 is formed from the two tubular (annular) members that are provided one behind the other to be in contact with and continuous with each other. Outer circumferential faces of the insulating ring 72a and the insulating tube 72b constituting the insulating frame 56 are in surface contact with the inner circumferential face of the observation window holding frame 20 and are glued and fixed with adhesive. As described above, since the insulating frame 56 is composed of two members, the insulating ring 72a and the insulating tube 72b, the insulating frame 56 can be easily molded even by using ceramic that is a member with low water absorption and is a sintered member hard to process and mold into a complicated shape. Note that the insulating frame 56 here may, of course, be formed of a resin member with low water absorption or may be molded by using different materials, such as ceramic and resin with low water absorption, for the insulating ring 72a and the insulating tube 72b.

(Second Modification of Insulating Member)

As shown in FIG. 19, in the insulating frame 56 for insulation and thermal insulation, a plurality of electrodes 73 for transmitting and receiving signals to and from and supplying power to the thermistor 54 and the anti-fogging device 52 of the anti-fogging unit 51 may be insert-molded using resin with low water absorption. With the configuration, the insulating frame 56 can reduce entry of moisture and air paths from a part where the plurality of electrodes 73 are provided.
(First Modification of Anti-Fogging Unit)

As shown in FIG. 20, in the anti-fogging unit 51, the device-insulating frame 55 need not be provided. Insulation may be ensured by keeping the anti-fogging device 52 out of contact with the observation window holding frame 20 made of metal, and an insulator film, an insulating coating 55*a* of parylene, may be molded on a surface of the anti-fogging device 52 by, for example, evaporation in order to prevent static electricity applied via the observation window holding frame 20 from falling on the anti-fogging device 52.
(First Modification of Static-Protective Member)

The conductive plate 60 constituting a static-protective member here only needs to have a corner portion in a shape of a pointed end on the front side. As shown in FIG. 21, the conductive plate 60 may be shaped to have a tapering conductive portion 60*b*.
(Second Modification of Static-Protective Member)

As shown in FIG. 22, the conductive plate 60 here may have a T-shape at a front portion and be shaped to have a conductive portion 60*c* on two sides of a distal end. The conductive plate 60 can be easily positioned by making T-shaped rear end portions 60*d* abut on the notched portion 56*c* of the insulating frame 56 when the conductive plate 60 is installed at and fixed to the insulating frame 56.
(Third Modification of Static-Protective Member)

As shown in FIG. 23, the conductive plate 60 here may have a T-shape at a front portion and be shaped to have a plurality of conductive portions 60*e* on a distal end side. The conductive plate 60 here can also be easily positioned by making T-shaped rear end portions 60*f* abut on the notched portion 56*c* of the insulating frame 56 when the conductive plate 60 is installed at and fixed to the insulating frame 56.
(Fourth Modification of Static-Protective Member)

As shown in FIG. 24, the conductive plate 60 here may be shaped such that a conductive portion 60*g* which is provided at a distal end part is curved upward.
(Fifth Modification of Static-Protective Member)

As shown in FIG. 25, instead of the conductive plate 60, a conductive block 74 made of metal which is a static-protective member may be provided at the insulating frame 56 such that the conductive block 74 is electrically continuous with the first lens holding frame 33.

More specifically, the conductive block 74 is fastened, with an adhesive 74*b*, to a hole portion 56*e* which is formed to penetrate through a part of the rib 56*a* of the insulating frame 56 from an outer circumferential portion to an inner circumferential portion. Note that a protrusion amount is set for a conductive portion 74*a* of the conductive block 74 such that the conductive portion 74*a* has a clearance of about 0.2 mm from the inner circumferential face of the observation window holding frame 20 and that the conductive portion 74*a* is arranged so as to protrude from the adhesive 74*b* toward the inner circumferential face of the observation window holding frame 20.

The conductive block 74 is disposed at the insulating frame 56 such that a bottom surface portion which is located on a side opposite from the conductive portion 74*a* is in contact with and electrically continuous with an outer circumferential face of the first lens holding frame 33.
(Sixth Modification of Static-Protective Member)

As shown in FIGS. 26 and 27, instead of the conductive plate 60, a conductive board 77 made of metal which is a static-protective member may be provided here at the insulating frame 56 so as to be electrically continuous with the first lens holding frame 33.

More specifically, the conductive board 77 is a disk-shaped metal plate which has, in an outer circumferential direction, a plurality of conductive portions 77*a* projecting radially. Note that the insulating frame 56 here is composed of two members identical in outer diameter, a ring-shaped insulating ring 75 which is arranged on the front side and a tubular insulating tube 76 which is arranged on the rear side.

The conductive board 77 is provided to be sandwiched between the insulating ring 75 and the insulating tube 76 of the insulating frame 56 and is fastened with an adhesive 78. Note that a protrusion amount is set for the conductive portions 77*a* of the conductive board 77 such that each conductive portion 77*a* has a clearance of about 0.2 mm from the inner circumferential face of the observation window holding frame 20 and that the conductive portions 77*a* are radially formed toward the inner circumferential face of the observation window holding frame 20. The conductive board 77 has a hole portion formed in a center, in which the first lens holding frame 33 is inserted, and is contact with and electrically continuous with the first lens holding frame 33.
(Action of Electronic Endoscope)

The electronic endoscope 1 with the above-described configuration is used in, for example, an endoscopic surgical operation. As shown in FIG. 28, the insertion portion 2 is introduced into a body cavity at about 37° C. and high humidity via a trocar 100 which is introduced in a body wall of a patient through perforation.

The electronic endoscope 1 is powered on in preparatory stages before introduction into the body cavity, and the anti-fogging device 52 of the anti-fogging unit 51 is driven. A voltage applied to the anti-fogging device 52 is 20 V here, as shown in FIG. 29. Temperature of the transparent cover member 22 serving as the observation window in an early phase of the preparatory stages, i.e., a temperature to be detected by the thermistor 54 is same as a room temperature of about 20° C. When the anti-fogging device 52 is driven upon power-on, the transparent cover member 22 requires a predetermined warm-up time period (of about 1 to 2 minutes) and is heated to, for example, 37° C. At power-on, as ambient temperature around the anti-fogging device 52 rises, the back surface of the transparent cover member 22 and an outer surface of the most distal end lens of the first group 32 of objective lenses can be prevented from fogging.

Note that driving and control of the anti-fogging device 52 is performed by control means in the video system center, to which a detected temperature value (an electrical resistance value corresponding to temperature) from the thermistor 54 is inputted. Note that a threshold value of 37° C. is set here for the detected temperature value from the thermistor 54 and that the control means controls driving to turn on/off the anti-fogging device 52 (see FIG. 29). With the configuration, heating temperature of the transparent cover member 22 is maintained at and around 37° C. during an intracavital insertion time period of the insertion portion 2 of the electronic endoscope 1. Note that control of the anti-fogging unit 51 by the control means in the video system center is ended upon power-off.

As described above, since the transparent cover member 22 is heated here to 37° C. during use, the electronic endoscope 1 can inhibit and prevent, e.g., fogging of and condensation on a surface of the transparent cover member 22 due to a temperature difference even if the electronic endoscope 1 is inserted into the body cavity at about 37° C. and high humidity.

(Action of Insulating Frame)

Action of the insulating frame 56 for insulation and thermal insulation will be described.

The insulating frame 56 has the insulating function illustrated in the above-described embodiment and, as shown in FIG. 30, a function of insulating heat so as not to uselessly transfer heat H of the anti-fogging device 52 of the anti-fogging unit 51 in preparatory stages to the first lens holding frame 33, the second lens holding frame 35, and the unit holding frame 36. That is, the heat H of the anti-fogging device 52 is efficiently and reliably transferred to the transparent cover member 22 via the device-insulating frame 55. With the function, the electronic endoscope 1 can have a shorter time period required for the transparent cover member 22 to reach the predetermined set temperature (37° C. here) in the preparatory stages than a conventional electronic endoscope.

During an endoscopic surgical operation (during the intracavital insertion time period), the insulating frame 56 for insulation and thermal insulation inhibits rearward transmission of heat via the first lens holding frame 33, the second lens holding frame 35, and the unit holding frame 36 through insulation of the heat H of the anti-fogging device 52 by the insulating frame 56 and prevents temperatures of the first image pickup device 42 and the second solid image pickup device 45 that are electronic components from increasing excessively.

It is thus possible to curb generation of noise due to increase in the temperatures of the first image pickup device 42 and the second solid image pickup device 45 and obtain a clear image. Since the heat H of the anti-fogging device 52 is inhibited by the insulating frame 56 from being uselessly transmitted to the first lens holding frame 33, the second lens holding frame 35, and the unit holding frame 36, the heat H is efficiently and reliably transferred to the transparent cover member 22 via the device-insulating frame 55. For the reason, in the electronic endoscope 1, the efficiency with which the transparent cover member 22 is heated by the anti-fogging device 52 improves, which improves anti-fogging efficiency.

As can be seen from the foregoing, the electronic endoscope 1 can inhibit thermal effects of the anti-fogging unit 51 on the solid image pickup devices and reduce noise to obtain a clear image, in addition to having the original insulating function. The electronic endoscope 1 can also provide the small-size image pickup unit which has improved efficiency in preventing fogging of the transparent cover member 22, the first group 32 of objective lenses, and the like that are objective optical systems by means of the anti-fogging unit 51. Note that similar effects can be achieved in the above-described configuration with the first or second modification of the insulating frame.

(GND System of Electronic Endoscope)

As shown in FIG. 31, the electronic endoscope 1 is configured such that the insertion portion 2 in front of the operation portion 3 as a boundary (an X axis in FIG. 31) and the universal cord 6 behind the operation portion 3 are electrically insulated from each other in a sheathed portion.

Note that, inside the electronic endoscope 1, the radiating cable 58 connected to the distal end rigid portion 23 made of metal is electrically connected to a metal frame 3a which is provided in the operation portion 3, as shown in FIG. 31. A capacitor 3d of, e.g., 220 pF is interposed between the metal frame 3a and a grip base 3b made of metal, and the metal frame 3a is insulated in a DC manner from the grip base 3b.

At least one of the three radiating cables 58 provided to extend from the image pickup unit 30 is electrically connected to the grip base of the operation portion 3. The three radiating cables 58 together with the signal cables 50 are integrally coated in a heat-shrinkable tube 80 which has a metal blade 80a inside. Note that the heat-shrinkable tube 80 is provided to extend to the grip base 3b, and the metal blade 80a is electrically connected to the grip base 3b.

Note that the universal cord 6 is connected to the grip base 3b in the operation portion 3 and that a metal sheath inside the universal cord 6 is electrically connected to the grip base 3b. The metal sheath of the universal cord 6 is electrically connected to a metal sheath of the communication cable 7 in the light guide connector 4. The light guide connector 4 and the video connector 5 are electrically connected to the individual metal sheaths of the universal cord 6 or the communication cable 7 and are each electrically connected to the patient GND via the light source apparatus or the video system center. That is, inner metal at the distal end of the electronic endoscope 1 is connected to the patient-side ground of the video connector 5 via the one radiating cable and the members on an operation portion proximal end side and is at a same potential as a potential of the patient-side ground.

(Action of Conductive Plate)

Action of the conductive plate 60 serving as the static-protective member will be described.

As shown in FIG. 32, the observation window holding frame 20 is located while a surface of an end portion on a front side which holds the transparent cover member 22 is exposed at a distal end face of the distal end portion 11. For the reason, static electricity E may be applied from the surface of the end portion of the observation window holding frame 20.

In the case, the static electricity E applied to the observation window holding frame 20 is aerially discharged, via the observation window holding frame 20, to the notched portion 56c of the insulating frame 56, i.e., the distal end corner portions (pointed edge portions) of the conductive plate 60 disposed with the clearance of 0.2 mm. The static electricity E then flows to the unit holding frame 36, to which the rear part of the conductive plate 60 is connected with the solder 60a, flows to the radiating cables 58 via the reinforcing frame 48, and is escaped (guided) to the patient GND.

With the configuration, even if the static electricity E is applied to the observation window holding frame 20 in the electronic endoscope 1, and an external portion and the inner metal are insulated in the endoscope insertion portion, the static electricity E does not flow to electronic components, such as the anti-fogging unit 51, the individual image pickup devices 42 and 45, and the individual image pickup drive circuits 43 and 46 and is guided from the conductive plate 60 to the patient GND via the unit holding frame 36, the reinforcing frame 48, and the radiating cables 58.

As can be seen from the foregoing, since static electricity applied to the endoscope distal end is aerially discharged to the conductive plate 60 and is escaped to the patient GND, the electronic endoscope 1 can prevent occurrence of trouble (e.g., a flow of excess current), a fault, and the like in electronic components, such as the anti-fogging unit 51, the individual image pickup devices 42 and 45, and the individual image pickup drive circuits 43 and 46, which are incorporated in the distal end portion 11. Note that similar effects can also be achieved in the above-described configuration with each of the first to sixth modifications of the static-protective member.

Note that although the electronic endoscope 1 described above has been illustrated in the context of a rigid endoscope for surgical medical treatments, the present invention is, of course, not limited to the endoscope. The present invention is a technique applicable to flexible endoscopes for various medical treatments or industrial endoscope apparatuses.

Reference Example 1

Reference Example 1 of the present invention will be described.

Figure 33:
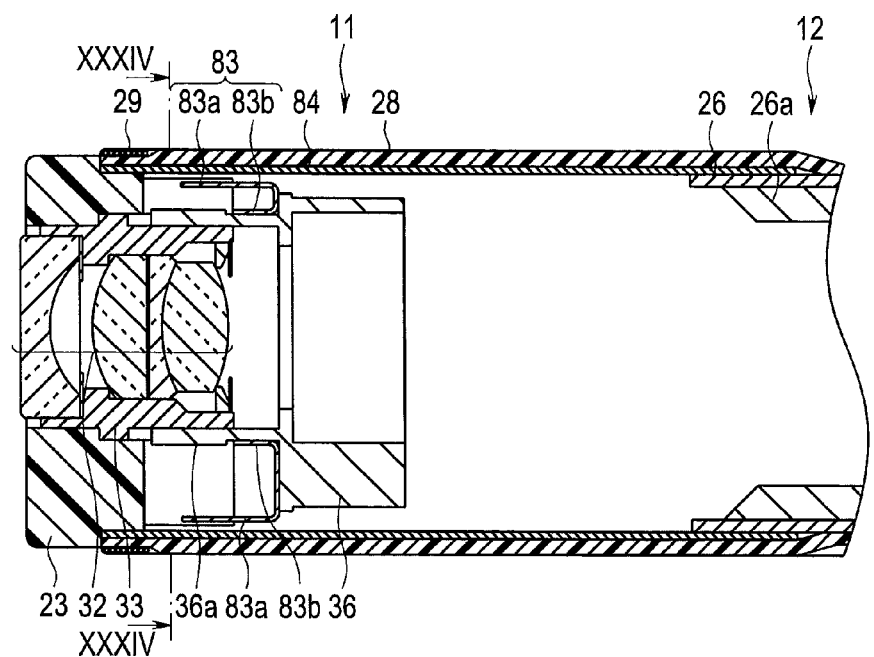
FIG. 33 is a cross-sectional view of a distal end part of an insertion portion according to Reference Example 1.
Figure 34:
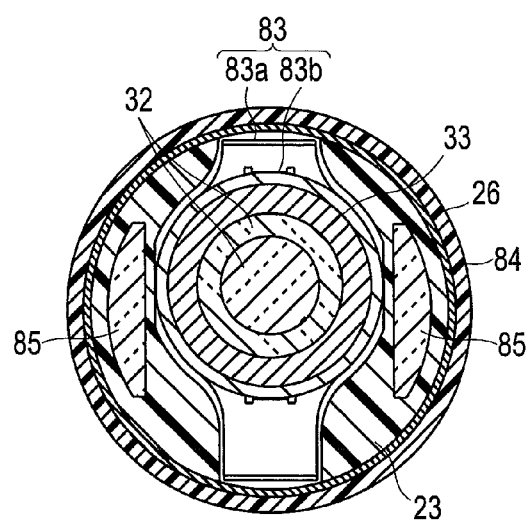
FIG. 34 is a cross-sectional view taken along line XXXIV-XXXIV in FIG. 33, according to Reference Example 1.
Figure 35:
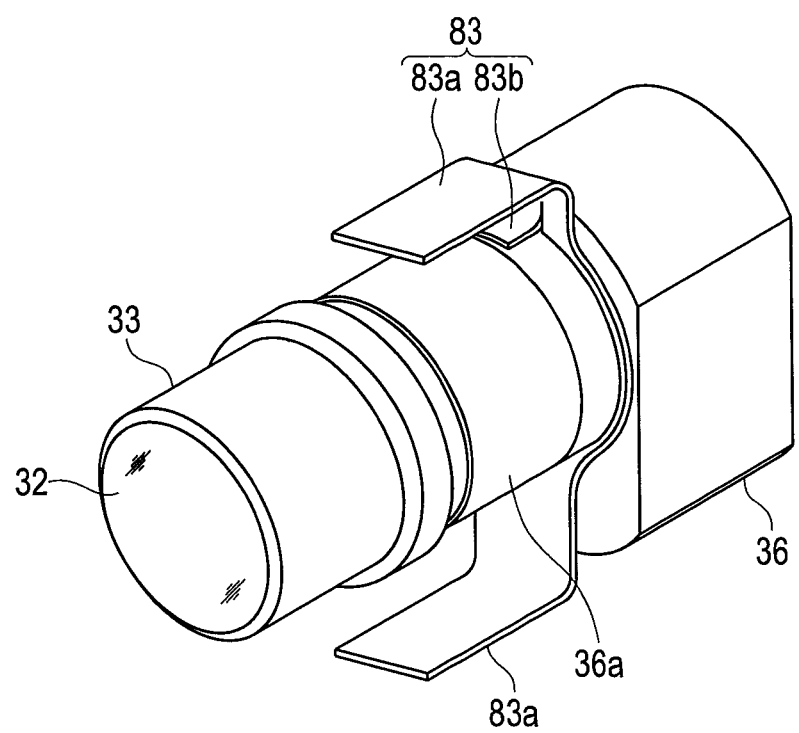
FIG. 35 is a perspective view showing a configuration of a conductive member which fits on a unit holding frame, according to Reference Example 1.
Figure 36:
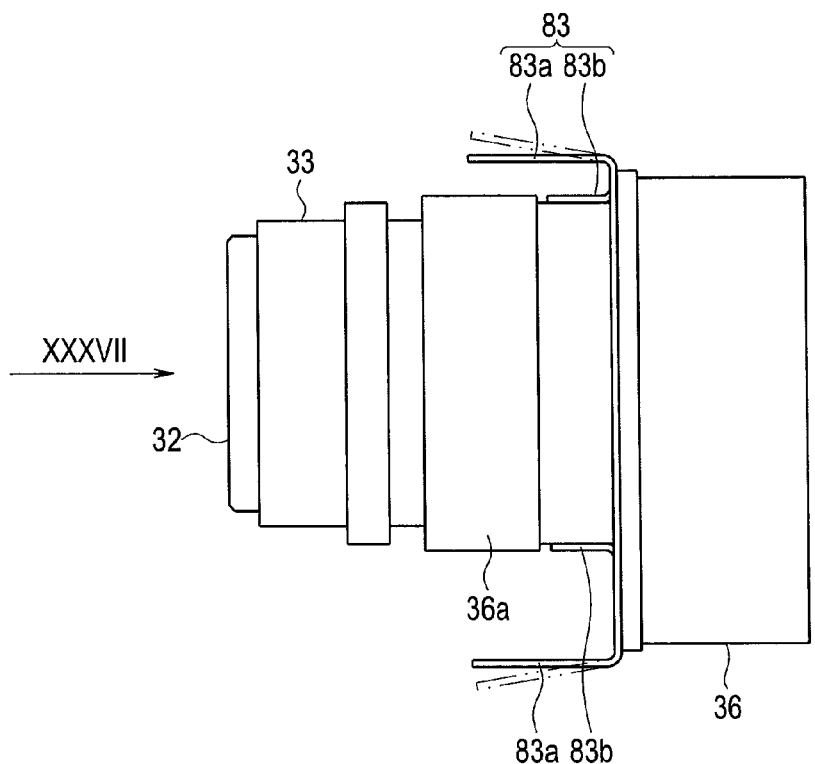
FIG. 36 is a side view showing the configuration of the conductive member which fits on the unit holding frame, according to Reference Example 1.
Figure 37:
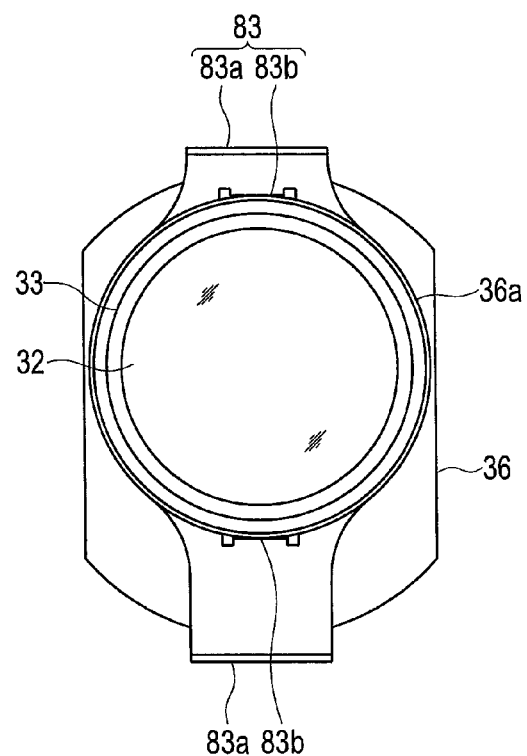
FIG. 37 is a view on arrow XXXVII in FIG. 36, according to Reference Example 1.
Figure 38:
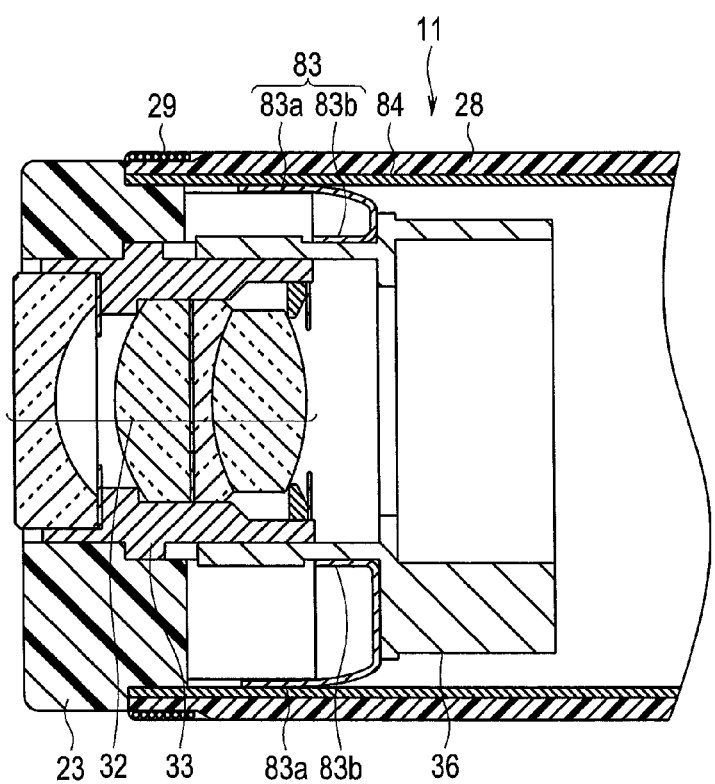
FIG. 38 is a cross-sectional view of the distal end part of the insertion portion according to a modification of Reference Example 1.

FIGS. 33 to 38 relate to Reference Example 1 of the present invention. FIG. 33 is a cross-sectional view of a distal end part of an insertion portion, FIG. 34 is a cross-sectional view taken along line XXXIV-XXXIV in FIG. 33, FIG. 35 is a perspective view showing a configuration of a conductive member which fits on a unit holding frame, FIG. 36 is a side view showing the configuration of the conductive member that fits on the unit holding frame, FIG. 37 is a view on arrow XXXVII in FIG. 36, and FIG. 38 is a cross-sectional view of the distal end part of the insertion portion according to a modification. Note that identical constituent components to the constituent components of the electronic endoscope 1 described above are denoted by identical reference numerals and that a detailed description of the constituent components will be omitted.

As shown in FIGS. 33 and 34, an electronic endoscope 1 here is coated in an insulative flexible tube 28 from a distal end portion 11 of an insertion portion 2 to an operation portion 3, and insulation of an outer circumference of the endoscope insertion portion which may contact a patient is ensured. Note that the electronic endoscope 1 is a flexible endoscope whose insertion portion 2 has flexibility. A distal end rigid portion 23 here is molded of, for example, resin and made of non-metal. Note that reference numeral 85 in FIG. 34 denotes a light guide bundle.

A unit holding frame 36 fits on a first lens holding frame 33 here. As shown in FIGS. 33 to 37, a conductive member 83 made of metal which is a static-protective member is provided in contact with the unit holding frame 36 such that the conductive member 83 is electrically connected to the unit holding frame 36.

More specifically, the conductive member 83 is a metal plate body having rectangular conductive portions 83*a* which are provided at two sites in a vertical direction to extend and are curved forward to have an L-shape in cross section and rectangular current-carrying contact portions 83*b* which are provided at two sites above and below a hole portion formed substantially in a center and are curved forward to have an L-shape in cross section.

The conductive member 83 is installed such that a cylindrical portion 36*a* of the unit holding frame 36 that fits on the first lens holding frame 33 is inserted to fit with the hole portion formed substantially in the center and such that a rear end face and the current-carrying contact portions 83*b* are in contact with and electrically connected to the unit holding frame 36. The conductive portions 83*a* of the conductive member 83 are arranged close to an inner circumferential face of a reinforcing frame 84 made of metal which fits with the distal end rigid portion 23 coated in the flexible tube 28. Although the conductive portions 83*a* and the reinforcing frame 84 are electrically continuous with each other, since the flexible tube 28 has electrical insulating properties, a clearance of 0.2 mm as illustrated in the above-described embodiment is unnecessary.

Note that the reinforcing frame 84 fits on a most distal end bending piece 26 which is disposed in a bending portion 12 of the insertion portion 2 in contact with the bending piece 26 and is electrically connected to the bending piece 26. Bending operation wires 26*a* are connected to the bending piece 26.

The first lens holding frame 33 is arranged here such that a surface of an end portion is exposed at a distal end face of the distal end portion 11. Static electricity may be applied from the surface of the end portion of the first lens holding frame 33. Static electricity applied to the first lens holding frame 33 flows to the unit holding frame 36 and flows to the reinforcing frame 84 via the conductive member 83.

That is, the static electricity flows from distal end corner portions (pointed edge portions) of each conductive portion 83*a* to the reinforcing frame 84 in contact with the conductive portions 83*a*. The static electricity flowing to the reinforcing frame 84 then flows to the bending operation wires 26*a* via the bending pieces 26. The bending operation wires 26*a* are electrically connected to a metal sheath of a universal cord 6 via a grip base 3*b* shown in FIG. 31 in the operation portion 3. The static electricity flowing through the metal sheath is escaped (guided) to a patient GND via a light guide connector 4 and a video connector 5.

With the above-described configuration, even if static electricity is applied to the first lens holding frame 33 in the electronic endoscope 1 here, the static electricity does not flow to electronic components, such as individual image pickup devices 42 and 45 and individual image pickup drive circuits 43 and 46, and are guided to the patient GND. Since applied static electricity is escaped to the patient GND, the electronic endoscope 1 here can prevent occurrence of trouble, a fault, and the like in the electronic components, such as the individual image pickup devices 42 and 45 and the individual image pickup drive circuits 43 and 46, incorporated in the distal end portion 11.

Note that the individual conductive portions 83*a* of the conductive member 83 may be configured so as to be elastically deformed in a diameter-increasing direction, as indicated by long dashed double-short dashed lines in FIG. 36, or may be configured so as to be in contact with the inner circumferential face of the reinforcing frame 84, as shown in FIG. 38. Alternatively, the individual conductive portions 83*a* may be soldered to the inner circumferential face of the reinforcing frame 84.

Reference Example 2

Reference Example 2 of the present invention will be described.

Figure 39:
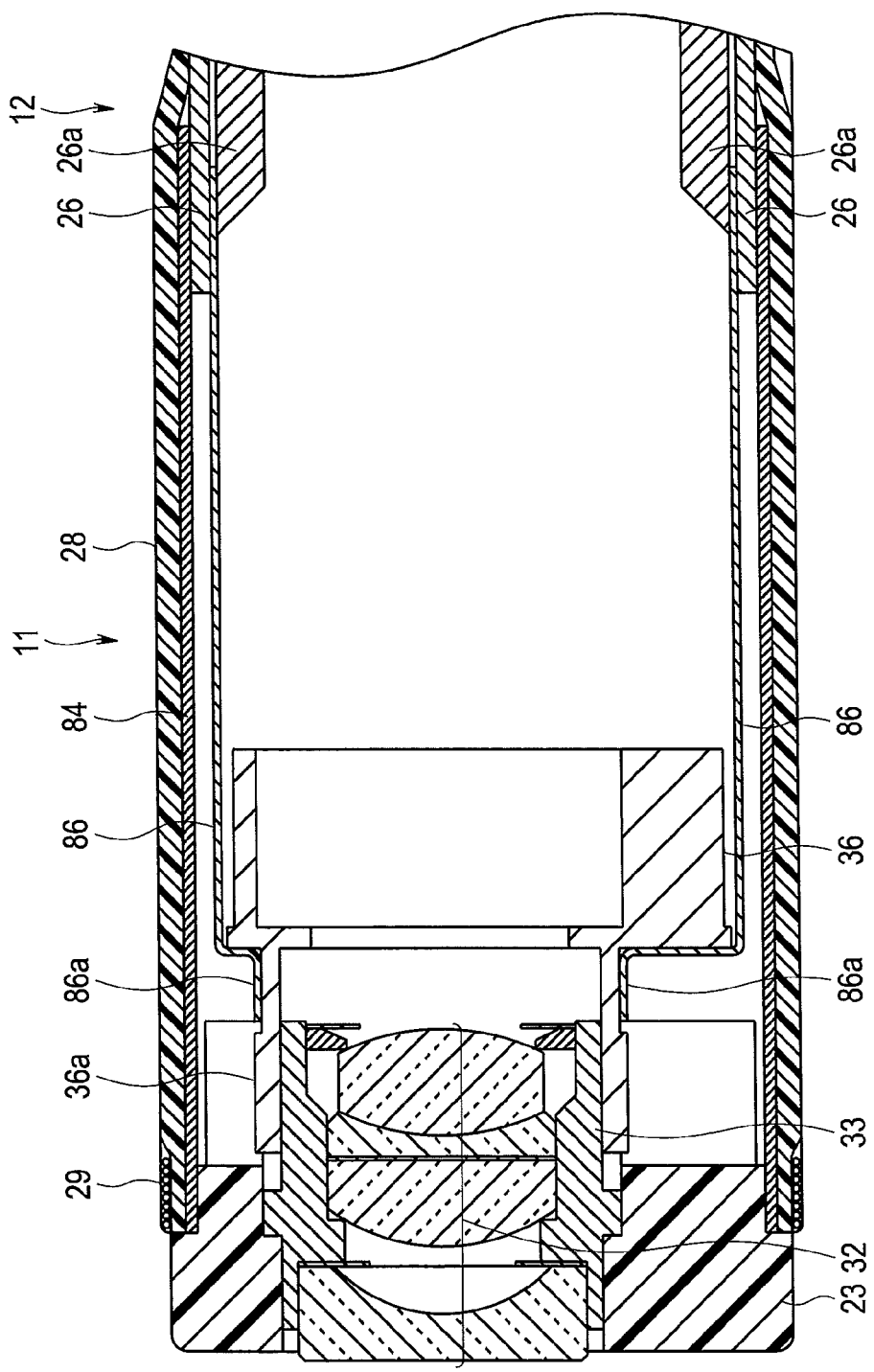
FIG. 39 is a cross-sectional view of a distal end part of an insertion portion according to Reference Example 2 of Reference Example 1.

FIG. 39 relates to Reference Example 2 of the present invention. FIG. 39 is a cross-sectional view of a distal end part of an insertion portion. Note that, in the present reference example as well, identical constituent components to the constituent components of the electronic endoscope 1 described above are denoted by identical reference numerals and that a detailed description of the constituent components will be omitted.

A conductive member 86 in a form of a metal plate which is a static-protective member is provided here in contact with a unit holding frame 36 such that the conductive member 86 is electrically connected to the unit holding frame 36. More specifically, two conductive members 86 are provided to be connected to two sites in a vertical direction of the unit holding frame 36. Respective distal end parts 86*a* in the conductive members 86 are soldered to a cylindrical portion 36*a* of the unit holding frame 36, and the conductive members 86 are electrically connected to the unit holding frame 36.

Rear end portions in the two conductive members 86 are each provided to be sandwiched between a most distal end bending piece 26 and a bending operation wire 26*a*, and the conductive members 86 are in contact with and electrically connected to the bending piece 26 and the bending operation wires 26*a*. The bending operation wires are connected to the bending piece 26.

Even with the above-described configuration, if static electricity is applied from a surface of an end portion of a first lens holding frame 33, the static electricity flows to the unit holding frame 36 and flows directly to the bending piece 26 and the bending operation wires 26a via the conductive members 86. The static electricity then passes through the bending operation wires 26a, a grip base 3b, a universal cord 6, and a communication cable 7 and is escaped (guided) to a patient GND via a light guide connector 4 and a video connector 5.

Since applied static electricity is escaped to the patient GND, an electronic endoscope 1 here can prevent occurrence of trouble, a fault, and the like in electronic components, such as individual image pickup devices 42 and 45 and individual image pickup drive circuits 43 and 46, incorporated in a distal end portion 11.

Reference Example 3

Reference Example 3 of the present invention will be described.

Figure 40:
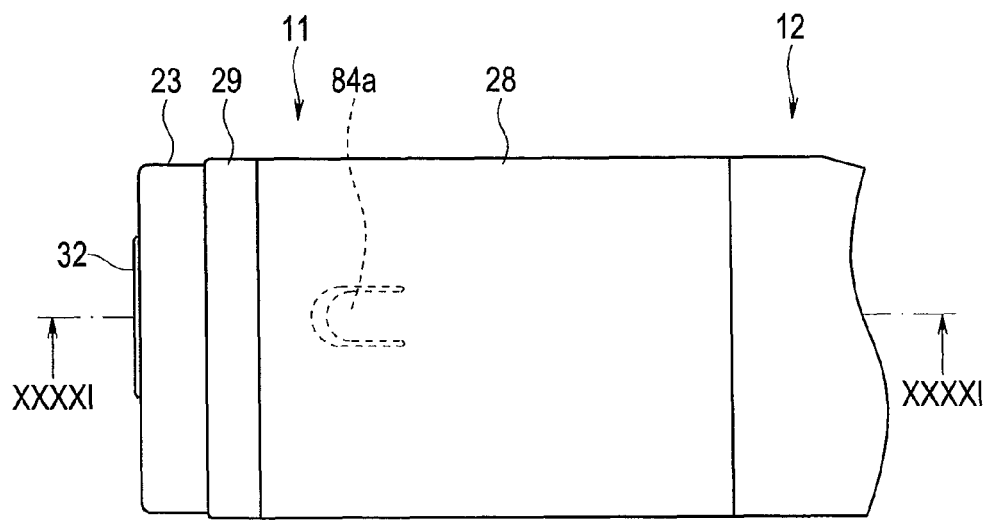
FIG. 40 is a plan view of a distal end part of an insertion portion according to Reference Example 3.
Figure 41:
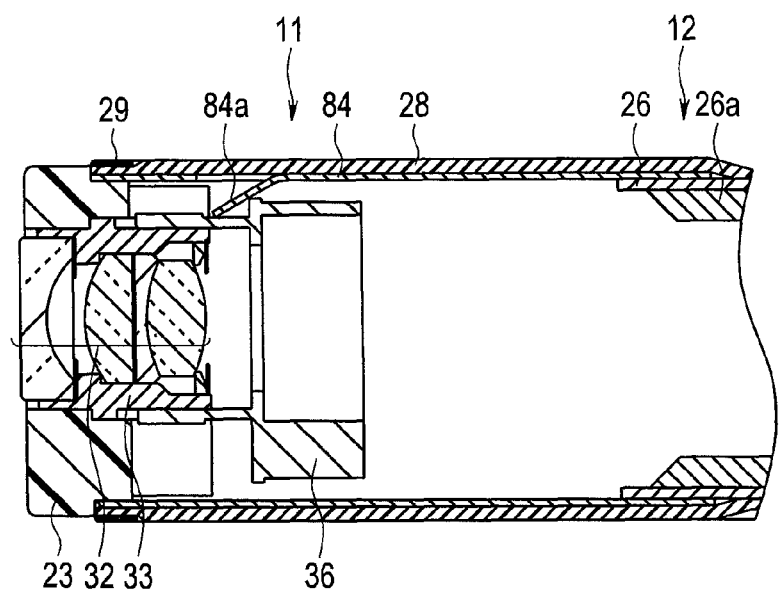
FIG. 41 is a cross-sectional view of the distal end part of the insertion portion according to Reference Example 3, taken along line XXXXI-XXXXI in FIG. 40.

FIGS. 40 and 41 relate to Reference Example 3 of the present invention. FIG. 40 is a plan view of a distal end part of an insertion portion, and FIG. 41 is a cross-sectional view taken along line XXXXI-XXXXI in FIG. 40. Note that, in the present reference example as well, identical constituent components to the constituent components of the electronic endoscope 1 described above are denoted by identical reference numerals and that a detailed description of the constituent components will be omitted.

As shown in FIGS. 40 and 41, a conductive piece 84a which serves as a static-protective member is formed by making an incision in a portion of a reinforcing frame 84, and the conductive piece 84a is curved toward a cylindrical portion 36a of a unit holding frame 36 to contact the cylindrical portion 36a. That is, the reinforcing frame 84 and the unit holding frame 36 are electrically connected via the conductive piece 84a. Note that after the conductive piece 84a is curved, the conductive piece 84a may be soldered to the cylindrical portion 36a of the unit holding frame 36.

Even with the above-described configuration, if static electricity is applied from a surface of an end portion of a first lens holding frame 33, the static electricity flows to the unit holding frame 36 and flows to the reinforcing frame 84 via the conductive piece 84a. The static electricity then flows from a bending piece 26 which fits with the reinforcing frame 84 to bending operation wires 26a. Accordingly, the static electricity passes through the bending operation wires 26a, a grip base 3b, a universal cord 6, and a communication cable 7 and is escaped (guided) to a patient GND via a light guide connector 4 and a video connector 5.

Since applied static electricity is escaped to the patient GND, the electronic endoscope 1 here can prevent occurrence of trouble, a fault, and the like in electronic components, such as individual image pickup devices 42 and 45 and individual image pickup drive circuits 43 and 46, incorporated in a distal end portion 11.

The invention described in the above-described embodiment is not limited to the embodiment and modifications. In practice, various modifications can be made without departing from scope of the invention. Additionally, the above-described embodiment includes various levels of inventions. Various inventions can thus be extracted by appropriately combining a plurality of constituent features disclosed.

For example, in the embodiment, an endoscope distal end is equipped with an anti-fogging device. An electronic component other than the anti-fogging device may, of course, be employed. Even if some constituent features are deleted from all constituent features, a configuration with the constituent features deleted can be extracted as an invention, provided that the problems described can be solved and that the effects described can be obtained.

What is claimed is:

1. An electronic endoscope in which a static-protective member is provided in a distal end portion of an insertion portion, the electronic endoscope comprising:
   the distal end portion of the insertion portion which incorporates electronic components;
   a metal frame which is disposed at the distal end portion and holds an observation window;
   an earth member which is connected to a patient-side ground of an external device; and
   the static-protective member which is disposed in the distal end portion to have a predetermined clearance from the metal frame and is electrically connected to the earth member to let static electricity applied to the distal end portion flow to the earth member, wherein
   the static-protective member is a metal plate body having a conductive portion in a shape of a pointed end which easily discharges the static electricity.

2. The electronic endoscope in which a static-protective member is provided in a distal end portion of an insertion portion according to claim 1, wherein the static-protective member is a metal disk in which a plurality of conductive portions, each having a pointed shape, that easily discharge the static electricity are formed to project in an outer circumferential direction.

3. The electronic endoscope in which a static-protective member is provided in a distal end portion of an insertion portion according to claim 1, wherein the conductive portion in the static-protective member is arranged, with a predetermined clearance from the metal frame, at an insulating member which is made to fit with the metal frame such that the static electricity is aerially discharged.

4. The electronic endoscope in which a static-protective member is provided in a distal end portion of an insertion portion according to claim 3, wherein an anti-fogging unit which has an anti-fogging device that is one of the electrical electronic components and prevents fogging of the observation window is disposed at the insulating member.

5. The electronic endoscope in which a static-protective member is provided in a distal end portion of an insertion portion according to claim 1, wherein the static-protective member is electrically connected to a lens holding frame which is arranged on a side, closer to a proximal end of the metal frame, of an image pickup unit incorporated in the distal end portion.

6. The electronic endoscope in which a static-protective member is provided in a distal end portion of an insertion portion according to claim 5, wherein
   the earth member is electrically connected to the lens holding frame, and
   the earth member is a radiating cable which radiates heat of the image pickup unit.

7. The electronic endoscope in which a static-protective member is provided in a distal end portion of an insertion portion according to claim 6, wherein
   the lens holding frame is electrically connected to a metal reinforcing frame which is insulated and arranged so as to cover a solid image pickup device and an image pickup drive circuit that are the electronic components, and
   the radiating cable is connected to the metal reinforcing frame.

* * * * *